US012758573B2

(12) United States Patent
Asanuma et al.

(10) Patent No.: US 12,758,573 B2
(45) Date of Patent: Oct. 13, 2026

(54) RNA ACTION INHIBITOR AND USE THEREOF

(71) Applicants: NATIONAL UNIVERSITY CORPORATION TOKAI NATIONAL HIGHER EDUCATION AND RESEARCH SYSTEM, Nagoya (JP); NICCA CHEMICAL CO., LTD., Fukui (JP); HOKKAIDO SYSTEM SCIENCE CO., LTD., Sapporo (JP)

(72) Inventors: Hiroyuki Asanuma, Nagoya (JP); Yukiko Kato, Nagoya (JP); Keiji Murayama, Nagoya (JP); Toshiki Tsuboi, Nagoya (JP); Tomohito Doke, Nagoya (JP); Takuji Ishimoto, Nagoya (JP); Shoichi Maruyama, Nagoya (JP); Toshio Kokuryo, Nagoya (JP); Ayako Koto, Fukui (JP); Isao Ishimaru, Fukui (JP); Ryoichi Asai, Fukui (JP); Ayaka Nakasha, Fukui (JP); Tomoe Sugita, Sapporo (JP); Keisuke Nishi, Sapporo (JP); Motoki Yuguchi, Sapporo (JP); Masanori Matsumoto, Sapporo (JP)

(73) Assignees: NATIONAL UNIVERSITY CORPORATION TOKAI, Nagoya (JP); NATIONAL HIGHER EDUCATION AND RESEARCH SYSTEM, Fukui (JP); NICCA CHEMICAL CO., LTD. HOKKAIDO SYSTEM SCIENCE CO., LTD., Sapporo (JP)

( * ) Notice: Subject to any disclaimer, the term of this patent is extended or adjusted under 35 U.S.C. 154(b) by 1118 days.

(21) Appl. No.: 17/637,707

(22) PCT Filed: Aug. 20, 2020

(86) PCT No.: PCT/JP2020/031513
§ 371 (c)(1),
(2) Date: Feb. 23, 2022

(87) PCT Pub. No.: WO2021/039598
PCT Pub. Date: Mar. 4, 2021

(65) Prior Publication Data
US 2022/0401466 A1 Dec. 22, 2022

(30) Foreign Application Priority Data
Aug. 23, 2019 (JP) ................................ 2019-153235

(51) Int. Cl.
*A61K 31/7115* (2006.01)
*C12N 15/113* (2010.01)

(52) U.S. Cl.
CPC ...... *A61K 31/7115* (2013.01); *C12N 15/1138* (2013.01)

(58) Field of Classification Search
None
See application file for complete search history.

(56) References Cited

U.S. PATENT DOCUMENTS

| | | | |
|---|---|---|---|
| 2008/0032282 | A1 | 2/2008 | Lin et al. |
| 2009/0104614 | A1 | 4/2009 | Tsourkas et al. |
| 2016/0304878 | A1 | 10/2016 | Chi et al. |

FOREIGN PATENT DOCUMENTS

| | | | |
|---|---|---|---|
| CN | 103255201 | A | 8/2013 |
| JP | 2009-536664 | A | 10/2009 |

(Continued)

OTHER PUBLICATIONS

Kokuryo, Toshio, et al. "NEK2 is an effective target for cancer therapy with potential to induce regression of multiple human malignancies." Anticancer research 39.5 (2019): 2251-2258. (Year: 2019).*

(Continued)

*Primary Examiner* — Brian Whiteman
*Assistant Examiner* — Khaleda B Hasan
(74) *Attorney, Agent, or Firm* — Oliff PLC

(57) ABSTRACT

An agent for inhibiting the action of a target RNA based on RNA interference and antisense oligonucleotide (ASO). The RNA interference agent includes a passenger strand and a guide strand for a target RNA. Both ends of double-stranded RNA formed pairing of the passenger and guide strands are blunt ends, and one or two or more of the units represented by formula (1) and formula (2) below are provided at the following positions (a) and (b): (a) 5' end side and 3' end side of the passenger strand, (b) 3' end side of the guide strand

[C1]

(1)

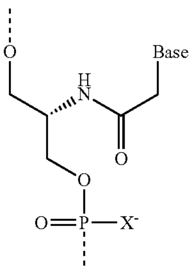

where X represents an oxygen atom or sulfur atom,

[C2]

(Continued)

-continued (2)

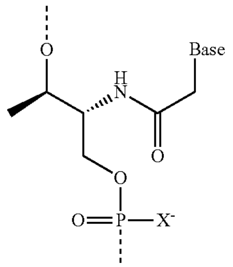

where X represents an oxygen atom or sulfur atom.

9 Claims, 24 Drawing Sheets

Specification includes a Sequence Listing.

(56) References Cited

FOREIGN PATENT DOCUMENTS

| | | |
|---|---|---|
| JP | 2016-130232 A | 7/2016 |
| JP | 2019/030312 A | 2/2019 |
| WO | 2007/143316 A2 | 12/2007 |

OTHER PUBLICATIONS

Jun. 21, 2024 Office Action issued in Chinese Patent Application No. 202080059161.1.

May 10, 2022 Office Action issued in Japanese Patent Application No. 2022-002855.

Mar. 19, 2024 Office Action Issued in Taiwanese Patent Application No. 109128644.

Sep. 13, 2022 Office Action issued in Japanese Patent Application No. 2022-002855.

Nov. 1, 2024 Office Action issued in Chinese Patent Application No. 202080059161.1.

Aug. 4, 2023 Office Action issued in Chinese Patent Application No. 202080059161.1.

Sep. 19, 2023 Search Report issued in European Patent Application No.20856865.9.

Le, Bao et al.; "Antisense oligonucleotide modified with serinol nucleic acid(SNA) induces exon skipping in mdx myotubes"; RSC Advances; Royal Society of Chemistry; vol. 7; No. 54; 2017; pp. 34049-34052.

Asanuma, Hiroyuki et al.; "De Novo Design of Functional Oligonucleotides with Acyclic Scaffolds"; The Chemical Record; The Chemical Society of Japan and Wiley-VCH, Weinheim; vol. 14; No. 6; 2014; pp. 1055-1069.

Benhida, Rachid et al.; "Incorporation of Serinol Derived Acyclic Nucleoside Analogues into Oligonucleotides: Influence on Duplex and Triplex Formation"; Tetrahedron Letters; vol. 39; 1998; pp. 6167-6170.

Kashida, Hiromu et al.; "Acyclic artificial nucleic acids with phosphodiester bonds exhibit unique functions"; Polymer Journal; vol. 48; No. 48; 2016; pp. 781-786.

Suzuki, Kazushi et al.; "Novel combination treatment for colorectal cancer using Nek2 siRNA and cisplatin"; Cancer Science; vol. 101; No. 5; 2010; pp. 1163-1169.

Alagia, Adele et al.; "Modulation of the RNA Interference Activity Using Central Mismatched siRNAs and Acyclic Threoninol Nucleic Acids (aTNA) Units"; Molecules; vol. 20; pp. 7602-7619, (2015).

Kamiya, Yukiko et al.; "Investigation of Strand-Selective Interaction of SNA-Modified siRNA with AGO2-MID"; International Journal of Molecular Sciences; vol. 21; 2020; p. 5218.

Kamiya, Yukiko et al., "Enhancement of Stability and Activity of siRNA by Terminal Substitution with Serinol Nucleic Acid (SNA).", ChemBioChem, (2014), vol. 15, pp. 2549-2555.

Kamiya, Yukiko et al., "Introduction of 2,6-Diaminopurines into Serinol Nucleic Acid Improves Anti-miRNA Performance.", ChemBioChem, (2017), vol. 18, pp. 1917-1922.

Murayama, Keiji et al., "Ultrasensitive Molecular Beacon Designed with Totally Serinol Nucleic Acid (SNA) for Monitoring mRNA in Cells.", ChemBioChem, (2015), vol. 16, pp. 1298-1301.

Asanuma, Hiroyuki, "Functional reinstallation of nucleic acids aiming for medical applications.", The 29th Banyu Sendai Symposium, https://www.msd-life-science-foundation.or.jp/banyu/wp-content/uploads/2018/04/2018 sendai05.pdf>,(2018).

Kokuryo, Toshio et al., "Nek2 siRNA therapy using a portal venous port-catheter system for liver metastasis in pancreatic cancer.", Cancer Science, (2016), vol. 107, No. 9, pp. 1315-1320.

Nov. 2, 2020 International Search Report issued in Patent Application No. PCT/JP2020/031513.

Nov. 2, 2020 Written Opinion of the International Searching Authority issued in Patent Application No. PCT/JP2020/031513.

Aug. 17, 2021 Office Action issued in Japanese Patent Application No. 2021-510484.

* cited by examiner

| | Urinary sugar (test paper method) |
|---|---|
| SNA | (2+)～(3+) |
| L-aTNA | (2+)～(3+) |
| 2'-MOE | (4+) |
| PBS | (-) |

FIG.11

Anti-miR21-MB: (*S*)-MMGCGTCDDCATCAGTCTGATDDGCTACGCY-(*R*)
(D:2,6-diaminopurine, M: Methylred, Y: Cy3, Underlined parts are stem regions )
miR21(target): 3'-aguuguagucagacuauucgau-5'
Anti-miR21-MB:SEQ NO: 21
miR21(target):SEQ NO: 22
*Double underline indicates sites having DD substituted for AA
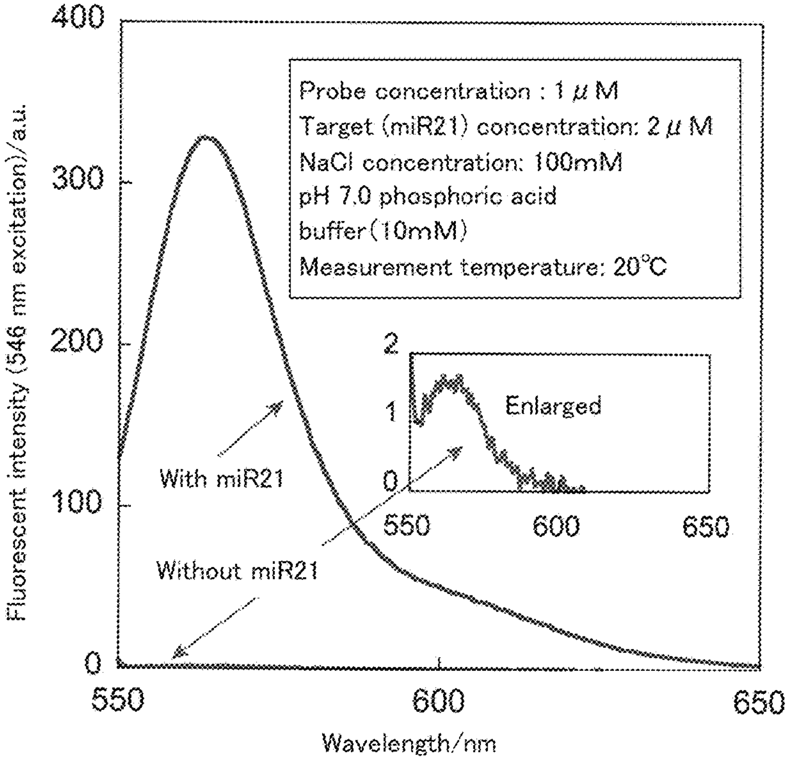
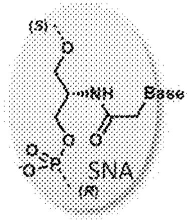
S/B ratio= 205>100
FIG.12

Detection minimum = 200 pM

Animals: C57BL6/J (Japan SLC), male, 9 to 10 weeks old
Drugs: 2'-MOE, PS, 2'-MOE2, SNA PS, SNA2
Dose: 10 mg/kg/dose, 3 times/week, total 10 doses
Administration route: Dissolved in PBS, subcutaneous injection

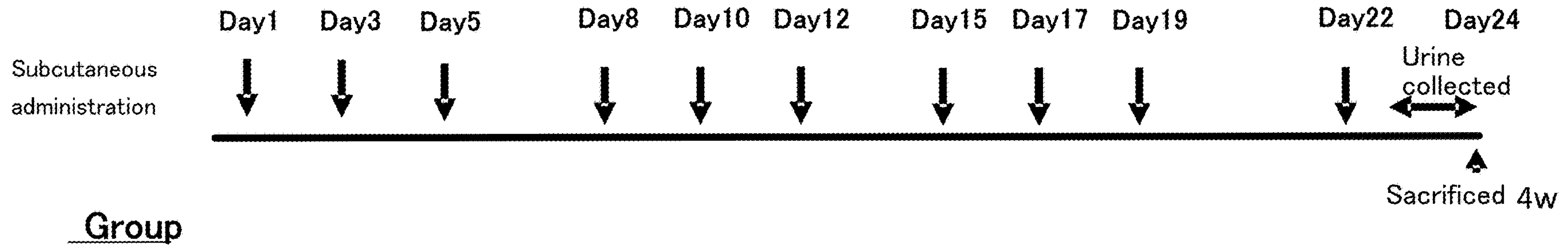

Group set1

- Antisense nucleic acid: SNA PS 10mg/kg/day
- Antisense nucleic acid: 2' MOE PS 10mg/kg/day set2

- Antisense nucleic acid: SNA2 10mg/kg/day
- Antisense nucleic acid: 2' MOE2 10mg/kg/day

- Control: Phosphate-buffered saline(PBS)

Evaluation items: Urinary sugar, kidney SGLT2 mRNA and protein, Liver function

FIG.14

Experimental Protocols

10mg/kg, twice Sustained experiment, DNA & SNA2 & SNA4

C57BL6(purchased from Japan SLC), male, 9 to 10 weeks old

Experimental Design

Group

- non treat ; PBS
- t reatment; DNA 10mg/kg/day
- t reatment; SNA2 10mg/kg/day
- t reatment; SNA4 10mg/kg/day Result(PCR) 0W 10mg/kg, twice Sustained experiment Result(PCR) 1W 10mg/kg, twice Sustained experiment Result(PCR) 2W 10mg/kg, twice Sustained experiment

RNA ACTION INHIBITOR AND USE THEREOF

The present application contains a Sequence Listing that has been submitted electronically in ASCII format and is hereby incorporated by reference in its entirety. The ASCII copy, created on Dec. 1, 2025, is named Substitute Sequence Listing_ST25.txt and is 4,912 bytes in size.

TECHNICAL FIELD

Cross-Reference to Related Applications

The priority claim for this application is based on Japanese Patent Application No. 2019-153235 filed on Aug. 23, 2019, and the entire contents of that application are incorporated by reference into the present application.

The present Description relates to a more practical RNA action inhibitor targeting RNA.

BACKGROUND ART

Progress is being made in the development of RNA drugs containing small-molecule RNA such as siRNA and antisense oligonucleotides (ASO) targeting RNA as active ingredients. Various chemical modifications of RNA have been attempted in an effort to increase the stability, delivery and the like of such RNA drugs in vivo (Patent Literature 1).

Patent Literature 1: Japanese Patent Application Publication No. 2019-30312

SUMMARY

Technical Problem

However, there has not yet been sufficient research into effective modes of chemical modification for improving nuclease resistance and the knockdown effects of RNA drugs. In the case of siRNA, off-target effects also need to be suppressed. The present Description provides an oligonucleotide with a chemically modified form that is more useful as a target RNA action inhibitor and the like based on RNA interference and ASO, as well as a use therefor and the like.

The inventors discovered that nuclease resistance could be improved while simultaneously suppressing off-target effects and enhancing on-target activity by using a constituent unit comprising a base analog attached via an amide bond to L-threoninol having a chain portion with 3 carbon atoms and or/a constituent unit comprising a base analog attached via an amide bond to serinol as a backbone element in place of ribose/deoxyribose in oligonucleotide, and introducing this constituent unit at the 3' end and 5' end of a double-stranded oligonucleotide constituting siRNA.

The inventors also discovered that an oligonucleotide having such a constituent unit could provide high antisense effects even in single-stranded RNA constituting an anti-miRNA oligonucleotide (AMO).

The inventors also discovered the utility of a gapmer having such a constituent unit.

Furthermore, the inventors discovered that a beacon probe having such a constituent unit or the like is useful for detecting miRNA.

The present Description provides the following means based on these findings.

<1> An RNA interference agent provided with a passenger strand and a guide strand for a target RNA, wherein both ends of double-stranded RNA formed by pairing of the passenger strand and the guide strand constitute blunt ends, and one or two or more selected from the group consisting of the units represented by formula (1) and formula (2) below are provided at the following (a) and (b):

(a) 5' end side and 3' end side of the passenger strand, (b) 3' end side of the guide strand

[C1]

(1)

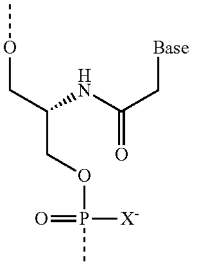

(in which X represents an oxygen atom or sulfur atom),

[C2]

(2)

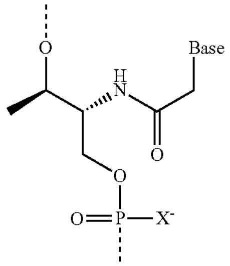

(in which X represents an oxygen atom or sulfur atom).

<2> The RNA interference agent according to <1>, wherein units represented by formula (2) are provided at (a), and a unit represented by formula (1) is provided at (b).

<3> The RNA interference agent according to <1> or <2>, wherein the units are of a kind and number that can improve one or two or more selected from the group consisting of RNase resistance, on-target activity and off-target suppression activity.

<4> The RNA interference agent according to any of <1> to <3>, for the purpose of suppressing expression of the NeK2 gene.

<5> A method for suppressing expression of a target gene, using an RNA double strand provided with a passenger strand and a guide strand for a target RNA, wherein both ends of double-stranded RNA formed by pairing of the passenger strand and the guide strand are blunt ends, and one or two or more selected from the group consisting of the units represented by formula (1) and formula (2) below are provided at the following (a) and (b):

(a) 5' end side and 3' end side of the passenger strand, (b) 3' end side of the guide strand.

[C3]

(1)

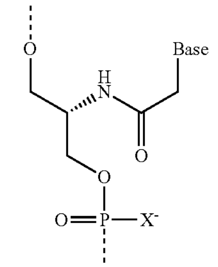

(in which X represents an oxygen atom or sulfur atom),

[C4]

(2)

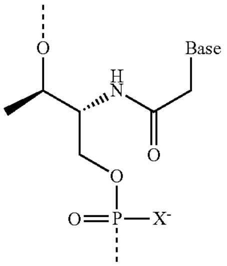

(in which X represents an oxygen atom or sulfur atom).

<6> An antisense nucleic acid provided with an antisense strand for a target RNA, wherein the antisense strand comprises a hybridizing region capable of hybridizing specifically with the target RNA and containing one or two or more selected from the group consisting of the units represented by formula (1) and formula (2) below:

[C5]

(1)

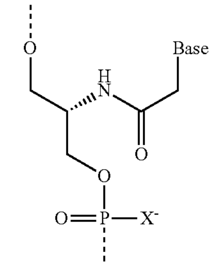

(in which X represents an oxygen atom or sulfur atom),

[C6]

(2)

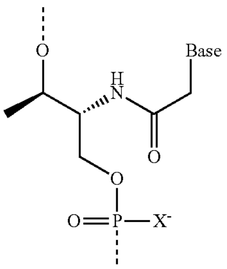

(in which X represents an oxygen atom or sulfur atom).

<7> The antisense nucleic acid according to <6>, wherein the target RNA is miRNA.

<8> An antisense nucleic acid provided with an antisense strand for a target RNA, wherein two side chains each containing one or two or more selected from the group consisting of the units represented by formula (1) and formula (2) below are provided at both ends of the antisense strand:

[C7]

(1)

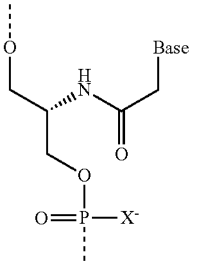

(in which X represents an oxygen atom or sulfur atom),

[C8]

(2)

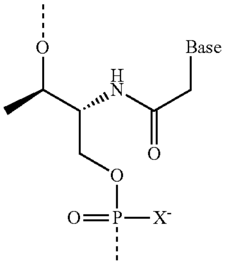

(in which X represents an oxygen atom or sulfur atom).

<9> A target RNA detection agent comprising a probe strand having a hybridizing region capable of hybridizing specifically with a target RNA and containing one or two or more selected from the group consisting of the units represented by formula (1) and formula (2) below, and also comprising a signal element for indicating that the probe strand has hybridized with the target RNA:

[C9]

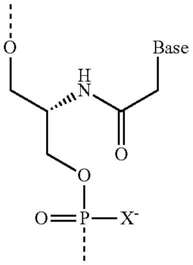

(1)

(in which X represents an oxygen atom or sulfur atom),

[C10]

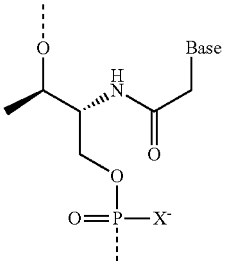

(2)

(in which X represents an oxygen atom or sulfur atom).

BRIEF DESCRIPTION OF DRAWINGS

FIG. 11 shows the results of an evaluation of increased urinary sugar excretion with the gapmer-type antisense nucleic acid prepared in the Second Embodiment;

FIG. 12 shows the fluorescence spectrum of the molecular beacon probe (SEQ ID NO: 21) prepared in the Fourth Embodiment during hybridization with target RNA (SEQ ID NO: 22);

FIG. 14 shows an outline of protocols for mouse administration testing using the gapmer-type antisense nucleic acid prepared in the Fifth Embodiment;

DESCRIPTION OF EMBODIMENTS

The disclosures of this Description relate to a more practical RNA action inhibitor targeting RNA. With the RNA interference agent disclosed in this Description, it is possible to provide an RNA interference agent that is highly practical in terms of improving nuclease resistance and on-target activity while simultaneously suppressing off-target effects.

Moreover, the ASO agent disclosed in this Description can contribute to improving the practicality of gapmers and AMOs, which are ASOs targeting miRNA.

In addition, the target RNA detection agent disclosed in this Description can also help improve the practicality of target RNA detection.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and inventions to provide a further improved RNA action inhibitor and use thereof.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the invention, separately from the constitution of features described in the Examples and/or Claims. Moreover, all descriptions of numerical ranges and groups or sets are intended to include intermediate configurations for purposes of restricting the initial disclosures and the claimed matter specifying the invention.

The disclosures of this Description are explained in detail below.

(RNA Interference Agent)

Figure 1:
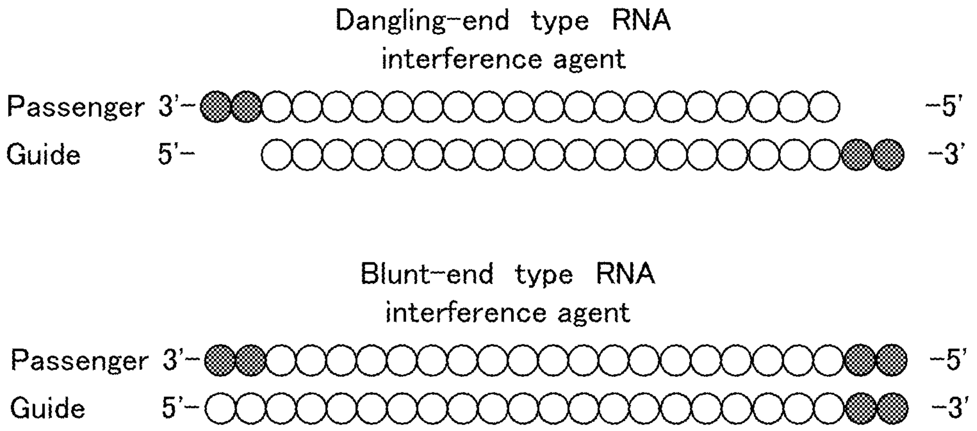
FIG. 1 shows one example of an RNA interference agent.

The RNA interference agent disclosed in this Description (hereunder sometimes simply called the RNA interference agent) is provided with a passenger strand and a guide strand for a target RNA and can have blunt ends at both ends of the double-stranded RNA formed by hybridization of these two strands. The structure shown in FIG. 1 for example may be adopted for this agent. In FIG. 1, each circle indicates a nucleotide, and the dark colored circles in particular indicate nucleotides referred to as the 3' end side and 5' end side.

The RNA targeted by the RNA interference agent is not particularly limited as long as it is RNA whose action is suppressed by RNA interference. Typical examples include non-coding RNA such as mRNA, pre-mRNA, miRNA and the like. The length of the recognition site for the target RNA is also not particularly limited but may be about 15-mer to 25-mer for example. The 5' end and 3' end of the passenger strand and the 3' end of the guide strand are all hydroxyl groups, while the 5' end of the guide strand is a phosphoric acid group or hydroxyl group.

Genes that cause cancer and various genetic disorders, genes associated with controlling expression of such genes, and various other regions can be selected appropriately as the target RNA. Examples of genes that can be targeted for cancer therapy include the NeK2 gene involved in pancreatic cancer for example.

(Passenger Strand)

The passenger strand of the RNA interference agent may have a nucleotide sequence roughly identical to the target RNA, or in other words a sense strand (SS). The length of the passenger strand is not particularly limited, and may be a length matching the target RNA, such as 17-mer to 27-mer for example. The length of the passenger strand may also be 18-mer to 25-mer for example, or 19-mer to 24-mer for example, or 20-mer to 23-mer for example. It may be identical to the length of the guide strand when it constitutes a blunt end through hybridization with the guide strand.

(3' End Side of Passenger Strand)

The nucleotide sequence of the 3' end side of the passenger strand is typically a sequence such as TT (thymine-thymine) comprised of pyrimidine bases such as thymine (T), uracil (U) and cytosine (C) or derivatives of these, but this is not a limitation, and other kinds of bases and modified bases may also be combined appropriately as long as the function of the RNA interference agent is retained. When the 3' end of the passenger strand is to be a blunt end in the RNA interference agent, complementarity with the nucleotide sequence of the 5' end side of the guide strand needs to be considered. The nucleotide sequence of the 5' end side of the guide strand is discussed below.

One or two or more selected from the group consisting of the units represented by formula (1) or formula (2) below (when both units are mentioned together, they are called the "unit of formula (1) or the like) as the backbone of the 3' end side of the passenger strand.

[C11]

(1)

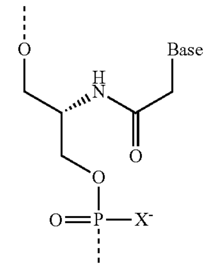

[C12]

(2)

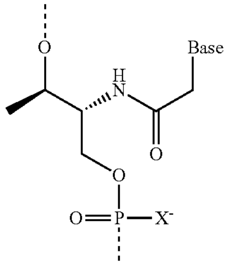

"Base" in formula (1) and formula (2) may indicate various known natural or artificial bases as appropriate. When X in formula (1) and formula (2) is an oxygen atom, it is bound to the 3' end side by a phosphodiester bond, while when X is a sulfur atom, it is bound to the 3' end side by a phosphorothioate bond.

For example one to four, or for example one to three, or for example one or two, or for example two of the unit represented by formula (1) or the like may be provided on the 3' end side of the passenger strand. The two or more units provided on the 3' end side may be the same kind of unit, or in other words may be all units represented by formula (1) or all units represented by formula (2), but units represented by formula (1) and formula (2) may also be combined, or units represented by formula (1) or formula (2) may be combined with natural nucleotides or other nucleoside derivatives.

One unit of formula (1) or the like may be provided at the end on the 3' end side of the passenger strand. When two or more units of formula (1) or the like are provided, about one or two units of formula (1) or the like may be provided continuously on the 5' end side of these terminal units.

(5' End Side of Passenger Strand)

The nucleotide sequence of the 5' end side of the passenger strand is not particularly limited, but when the RNA interference agent forms a blunt end at the 5' end of the passenger strand, complementarity with the nucleotide sequence of the 3' end side of the guide strand is taken into consideration. The nucleotide sequence of the 3' end side of the guide strand is explained below.

The backbone part on the 5' end side of the passenger strand may have one or two or more of the units represented by formula (1) or the like. For example, one to four, or for example one to three, or for example one or two, or for example two of the units of formula (1) or the like may be provided on this 5' end side. The two or more units provided on the 5' end side may be the same kind of unit, or in other words may be all units represented by formula (1) or all units represented by formula (2), but units represented by formula (1) and formula (2) may also be combined, or units represented by formula (1) or formula (2) may be combined with natural nucleotides or other nucleoside derivatives.

One unit of formula (1) or the like may be provided at the end on the 5' end side of the passenger strand. When two or more units of formula (1) or the like are provided, about one or two units of formula (1) or the like may be provided continuously on the 3' end side of these terminal units.

(Guide Strand)

The guide strand of the RNA interference agent may generally constitute a nucleotide sequence complementary to the nucleotide sequence of the target RNA and capable of hybridizing with the target RNA, or in other words an antisense (AS) strand. The length of the guide strand is not particularly limited, and may be a length matching the target RNA, such as 17-mer to 27-mer for example. The length of the guide strand may also be 18-mer to 25-mer for example, or 19-mer to 24-mer for example, or 20-mer to 23-mer for example.

(3' End Side of Guide Strand)

The nucleotide sequence of the 3' end side of the guide strand is typically a sequence such as TT (thymine-thymine) comprised of pyrimidine bases such as thymine (T), uracil (U) and cytosine (C) or derivatives of these, but other kinds of bases and modified bases may also be combined appropriately as long as the function of the RNA interference agent is retained.

A sequence complementary to a target mRNA may be used as the nucleotide sequence of the 3' end side of the guide strand. As a result, it may be constituted with thymine (T) or uracil (U) or derivatives of these as bases for example. Natural base pairs such as TA and UA or similar base pairs may be formed between the 3' end side of the guide strand and the 5' end side of the passenger strand. For example, T or U may be provided at the 3' end of the guide strand. More specifically, T may be provided at the 3' end of the guide strand for example, with another T (TT, indicating two bases from the 3' end) or another U (TU, indicating two bases from the 3' end) on the 5' end side thereof.

The backbone part on the 3' end side of the guide strand of the RNA interference agent may have for example one or two or more selected from the group consisting of the units represented by formula (1) and the like. For example, one to four, or for example one to three, or for example one or two, or for example two of the units of formula (1) or the like may be provided at the 3' end of the guide strand. The two or more units provided at the 3' end may be the same kind of unit, or in other words may be all units represented by formula (1) or all units represented by formula (2), but units represented by formula (1) and formula (2) may also be combined, or a unit represented by formula (1) or formula (2) may be combined with natural nucleotides or other nucleoside derivatives.

One or two or more selected from the group consisting of the units represented by formula (1) and the like may be provided at the end on the 3' end side of the guide strand. When two or more units represented by formula (1) and the like are provided, about one or two units represented by formula (1) and the like may be provided continuously on the 5' end side of these terminal units.

(5' End Side of Guide Strand)

The nucleotide sequence of the 5' end side of the guide strand is not particularly limited, and other kinds of bases or modified bases may be combined appropriately as long as the function of the RNA interference agent is retained.

The nucleotide sequence of the 5' end side of the guide strand is constituted for example with bases such as cytosine (C) or uracil (U), or derivatives of these. The 5' end side of the guide strand is made complementary to the nucleotide sequence of the 3' end side of the passenger strand. Consequently, a natural base pair such as AU or CG or a similar base pair may be formed on the 5' end side. For example, C or U may be provided on the 5' end side of the guide strand. More specifically, U may be provided on the 5' end of the guide strand for example, and C may be provided on the 3' end side of that C (UC, indicating 2 bases from the 5' end).

The backbone part on the 5' end side of the guide strand may be provided with a unit derived from a natural ribonucleotide or derivative thereof. This facilitates the selective incorporation of RISC at the 5' end of the guide strand and allows off-target effects to be suppressed. As in the case of the 3' end side, a unit represented by formula (1) or the like may also be provided. The 5' end of the guide strand is preferably phosphorylated.

Apart from the structures of both end sides as described above, the passenger strand and the guide strand of the RNA interference agent may also be provided as appropriate with nucleosides or nucleoside derivatives having natural or chemically modified bases and backbones of natural ribose or 2' chemically modified ribose. Binding of each nucleoside or nucleoside derivative may be by phosphodiester bonds or phosphorothioate bonds. In addition, the passenger strand and the guide strand may also have known chemical modifications as appropriate.

By providing the unit represented by formula (1) or the like on the 3' end sides and/or 5' end side constituting the blunt ends of the RNA interference agent, it is possible to effectively improve RNase resistance, on-target activity and off-target effect suppression activity. In particular, all of these actions can be effectively improved by providing units represented by formula (1) or the like on the 3' and 5' end sides of the passenger strand and the 3' end side of the guide strand.

Preferably the passenger strand and the guide strand in the RNA interference agent are each 22-mer to 24-mer strands forming blunt end structures at both ends, and both the 3' end side and the 5' end side of the passenger strand are provided at the ends with one or two continuous units represented by formula (1) or the like (consisting for example only of units represented by formula (2), or only of units represented by formula (1), or of a combination of units represented by formula (1) and units represented by formula (2)). Furthermore, the nucleotide sequence on the 3' end side of the passenger strand is AG for example from the end of the strand, while the nucleotide sequence on the 5' end side is AA for example from the end of the strand. Also, the 3' end side of the guide strand has one or two continuous unit represented by formula (1) or the like at the end of the strand. Furthermore, the nucleotide sequence on the 3' end side of the guide strand is TT or TU for example from the end of the strand, while the nucleotide sequence on the 5' end side is UC for example from the end of the strand.

Furthermore, for example the units represented by formula (1) and the units represented by formula (2) on the end sides of each strand of the RNA interference agent may consist of one kind of unit, or a combination of both kinds of unit. For example, this may take various forms such as a hybrid form in which the units represented by formula (1) and units represented by formula (2) are paired between the passenger strand and the guide strand, a chimera form in which both kinds of units are present in the passenger strand or the guide strand, or a mixed form combining the hybrid and chimera forms.

The RNA interference agent may be used for example as a drug for suppressing the expression of a gene associated with disease and may also be used for research applications. In the case of pharmaceutical applications, a suitable administration route such as intravenous administration, subcutaneously administration, cerebroventricular administration, nasal administration or intraperitoneal administration using elements for DDS can be selected appropriately according to the type of disease and the target site.

(Method for Suppressing Gene Expression)

The present Description also provides a method for using double-stranded RNA constituting the RNA interference agent to suppress expression of a gene. When the RNA interference agent is administered in vitro or in vivo, the RNA interference agent acts on target RNA inside mammalian cells, and the target RNA is decomposed or the like by RNA interference. This suppresses the action of the target RNA, typically by suppressing translation of mRNA into proteins, and gene expression is suppressed as a result. When the suppression method is used in vivo, it is used in non-human mammals for example.

The double-stranded RNA constituting the RNA interference agent can be obtained by known RNA synthesis methods. The units represented by formula (1) and formula (2) and oligonucleotides having these units can be synthesized in accordance with Japanese Patent Application Publication No. 2016-130232, Japanese Patent Application Publication No. 2011-135824 and the like for example.

(Target Nucleic Acid Detection Agent)

The target nucleic acid detection agent disclosed in this Description (hereunder sometimes called the detection agent) may be provided with a probe strand that contains one or two or more selected from the group consisting of the units represented by formula (1) and the like and has a hybridizing region capable of hybridizing specifically with a target nucleic acid, together with a signal element that indicates that the probe strand has hybridized with the target nucleic acid. A target nucleic acid can be detected sensitively in cells with this detection agent.

There are no particular limitations to the target nucleic acid targeted by this detection agent. It may be either DNA or RNA. When the target nucleic acid is DNA, specific regions of specific genes and mutations such as SNPs may be targeted. When the target nucleic acid is RNA, it may be non-coding RNA such as mRNA, pre-mRNA, miRNA or the like. The sequence length of the target nucleic acid is not particularly limited but may be about 4-mer to 25-mer for example.

The probe strand in the detection agent has a hybridizing region that hybridizes specifically with a target nucleic acid. The hybridizing region may have a length matching the sequence of the target nucleic acid. The entire length of the probe strand may be about 15-mer to 35-mer for example. The backbone constituting the hybridizing region is made up of units represented by formula (1) and the like for example. This allows it to hybridize highly specifically with a target RNA and to detect even mutations such as SNPs with high specificity for example. In addition to the hybridizing region, the stem-forming region may also be made up of units represented by formula (1) as discussed below.

The probe strand comprises one or two or more signal elements. The signal elements are not particularly limited, but for example may consist of a combination of a fluorescent dye and a quenching dye, so that when the probe strand is not hybridizing with a target nucleic acid, the fluorescent dye is quenched by the quenching dye, while when the probe strand has hybridized with a target nucleic acid, the fluorescent dye provides a signal. The compounds described in Japanese Patent Application Publication No. 2012-170373, Republished International Patent Publication No. 2011/105610 and Japanese Patent Application Publication No. 2013-78298 for example or other known compounds may be combined appropriately and used as the combination of fluorescent dye and quenching dye.

Such a fluorescent dye and quenching dye may be provided in various forms relative to the hybridizing region. One example is a molecular beacon in which at least part of the hybridizing region forms a loop, and the fluorescent dye and quenching dye are included in a stem-forming region. However, the hybridizing region may also extend to part of the stem-forming region. In this case, the fluorescent dye is disposed on the stem-forming region at one end of the single-stranded probe strand, and the quenching dye is disposed on the stem-forming region at the other end. When the fluorescent dye and quenching dye are provided on the stem-forming region, these may be provided at each end of the stem-forming region.

On the other hand, if for example the probe strand is constituted overall with a hairpin portion and a single-stranded portion extending from one end of the hairpin portion in a steady state, so that the hairpin opens when the hybridizing region hybridizes with a target nucleic acid, the fluorescent dye and quenching dye can be disposed on the hairpin-forming region of the probe strand.

The detection agent may be provided with one or two or more units having a 2,6-diaminopurine base in place of adenine (A) at a site that recognizes target DNA or RNA. By providing this base, it is possible to facilitate hairpin opening and increase fluorescent intensity by stabilizing the double strand when recognizing target DNA or RNA, thereby improving the signal(S) to background (B) ratio and also improving the detection sensitivity (detection limit) of the detection agent. When this base is provided, the S/B ratio may be at least 100 for example, or at least 150 for example, or at least 180 for example, or at least 190 for example, or at least 200 for example. The number of units having this base may be one to four for example, or one to three for example, or one or two for example.

When the probe strand constitutes a molecular beacon or a probe having a hairpin part, this base is preferably provided near the two stem-forming regions or the hairpin-forming regions having the fluorescent dye and the quenching dye. A unit having this base is positioned so as not to impede hybridization by the hybridizing region.

Like the RNA interference agent, the detection agent can be obtained by known DNA synthesis methods. The units represented by formula (1) and formula (2) and an oligonucleotide having these units can be synthesized in accordance with Japanese Patent Application Publication No. 2016-130232, Japanese Patent Application Publication No. 2011-135824 and the like.

(Gapmer-Type Antisense Oligonucleotide Agent)

The gapmer-type antisense oligonucleotide agent disclosed in this Description (hereunder sometimes called simply the antisense agent) may be provided with an antisense strand for a target RNA and side chains each containing one or two or more selected from the group consisting of the units represented by formula (1) and the like at both ends of the antisense strand.

The RNA targeted by the antisense agent is not particularly limited, but examples include non-coding RNA such as mRNA, pre-mRNA and miRNA. The length of the recognition site for the target nucleic acid is also not particularly limited and may be about 6-mer to 30-mer for example.

The antisense strand may have a nucleotide sequence capable of hybridizing specifically with the target RNA. The backbone part of this antisense strand may be formed of DNA. The nucleotides of the backbone part of this antisense strand may include phosphodiester bonds but may also be bound by phosphorothioate bonds. When the antisense strand includes CG, the 5' position of the C (cytosine) may be methylated to suppress TLR9 activation.

The antisense agent may be provided with side chains containing one or two or more of the units represented by formula (1) and the like at both ends of the antisense strand. The length of the side chains is not particularly limited but may be about 1-mer to 15-mer for example, or about 1-mer to 10-mer for example, or about 1-mer to 8-mer for example, or about 1-mer to 6-mer for example, or about 1-mer to 4-mer for example. The number of units represented by formula (1) or the like in these side chains is not particularly limited, and other nucleotide units may also be included.

The nucleotide structure of the side chains is not particularly limited, and for example nucleotide sequences complementary to the nucleotide sequences at both ends of the target RNA may be adopted. The side chains and the antisense strand may be joined by phosphorothioate bonds, and the units in the side chain may also be joined by phosphorothioate bonds.

Like the RNA interference agent, the antisense agent can be obtained by known DNA synthesis methods. The units represented by formula (1) and formula (2) and an oligonucleotide having these units can be synthesized in accordance with Japanese Patent Application Publication No. 2016-130232, Japanese Patent Application Publication No. 2011-135824 and the like.

EMBODIMENTS

Concrete embodiments of the disclosures of this Description are disclosed below, but these are intended to explain the disclosures of this Description and not to limit their scope.

First Embodiment (Preparation and Evaluation of NeK2-RNA Interference Agent)

The serine-threonine kinase Nek2 is a protein associated with cell proliferation that is known to be overexpressed in pancreatic cancer cells. NeK2 is therefore a promising target for pancreatic cancer treatment. In this embodiment, an RNA interference agent was prepared targeting mRNA of the Nek2 gene as target RNA.

The sequence of the target RNA of the RNA interference agent is based on a nucleotide sequence used in published literature (Kokuryo et al., Cancer Sci., 2016, 107, 1315-1320). RNA interference agents were designed as blunt end type RNA interference agents with the unit (SNA) represented by the following formula (3) and the unit (L-αTNA) represented by the following formula (4) substituted at the three ends apart from the 5' end of the guide strand. The nucleotide sequence and the mode of substitution of the units are shown in the following table.

TABLE 1

| | | | SEQ NO: |
|---|---|---|---|
| siNeK2 | Passenger | 3'-dT dT U G A A G C A G A C A C C G U A A G G -5' | 1 |
| | Guide | 5'- A C U U C G U C U G U G G C A U U C C dT dT -3' | 2 |
| siNeK2-S1 | Passenger | 3'- α G U G A A G C A G A C A C C G U A A G G A α -5' | 3 |
| | Guide | 5'-pU C A C U U C G U C U G U G G C A U U C C U t -3' | 4 |
| siNeK2-S2 | Passenger | 3'- α g U G A A G C A G A C A C C G U A A G G a a -5' | 5 |
| | Guide | 5'-pU C A C U U C G U C U G U G G C A U U C C t t -3' | 6 |
| siNeK2-T1 | Passenger | 3'- $\underline{A}$ G U G A A G C A G A C A C C G U A A G G A $\underline{A}$ -5' | 7 |
| | Guide | 5'-pU C A C U U C G U C U G U G G C A U U C C U $\underline{T}$ -3' | 8 |
| siNeK2-T2 | Passenger | 3'- $\underline{A}$ $\underline{G}$ U G A A G C A G A C A C C G U A A G G $\underline{A}$ $\underline{A}$ -5' | 9 |
| | Guide | 5'-pU C A C U U C G U C U G U G G C A U U C C $\underline{T}$ $\underline{T}$ -3' | 10 |

x = SNA,
$\underline{X}$ = L-αTNA

[C13]

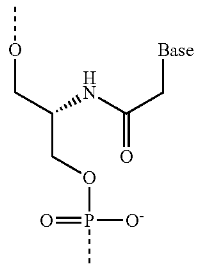

(3)

-continued

[C14]

(4)

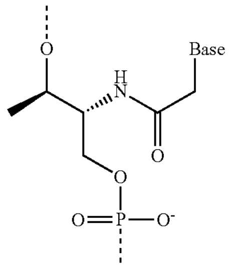

Figure 2:
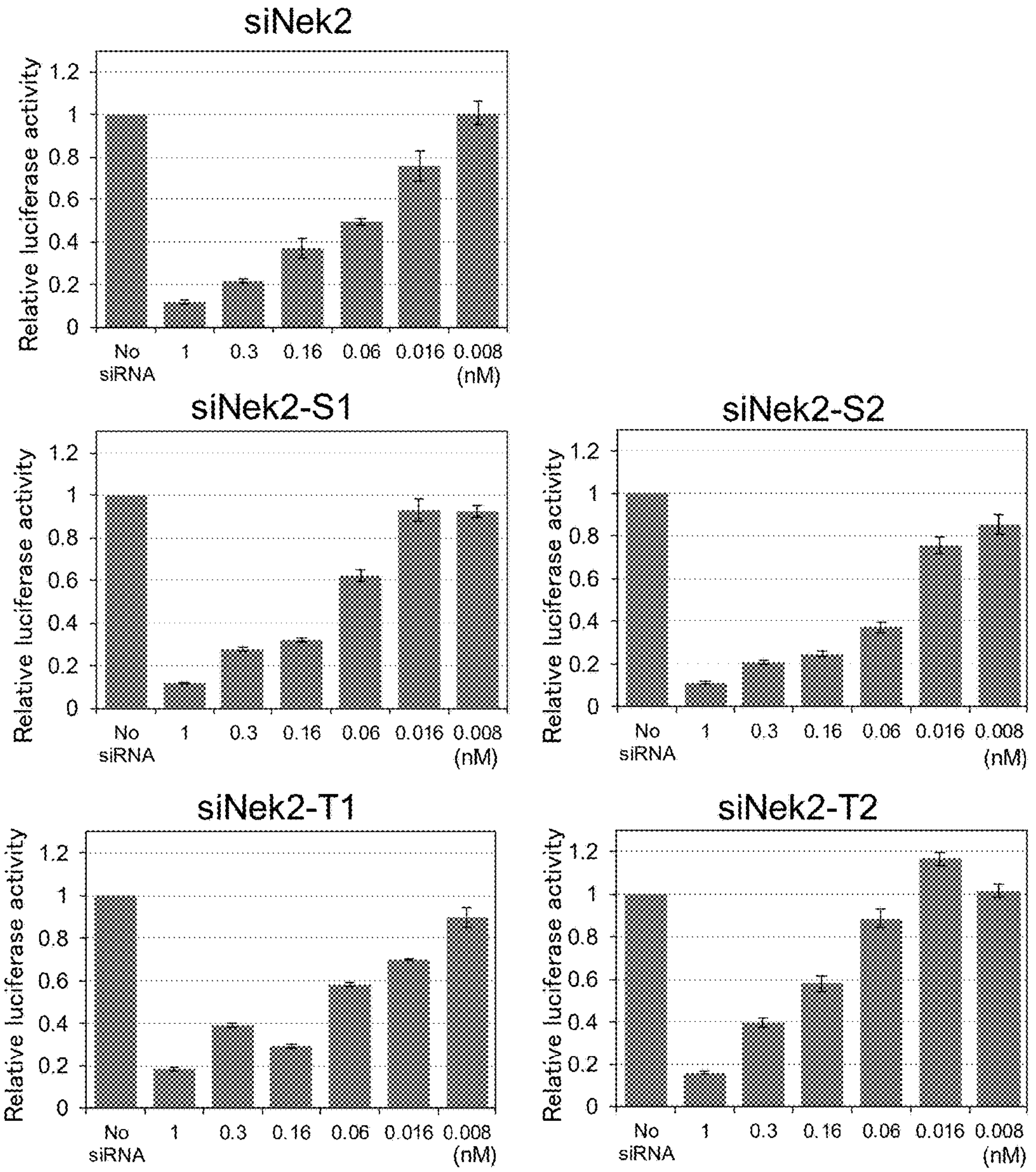
FIG. 2 shows the results of an evaluation (luciferase assay) of RNA interference by the RNA interference agent prepared in the First Embodiment.

The prepared RNA interference agents and a pmiR-Nek2 plasmid were transfected with LIPOFECTAMINE™ 2000 (Nucleic acid delivery reagent containing lipid nanoparticles) into HeLa cells that had been seeded on a 96-well plate. 48 hours after transfection, a luciferase assay was conducted using a DUAL-GLO™ luciferase assay system (Promega) (System for measuring luciferase activities of fireflies and sea squirts (*Renilla*)). The results are shown in FIG. 2. As shown in FIG. 2, all of the prepared RNA interference agents exhibited RNAi activity equivalent to that of an RNA interference agent (SiNek2) constituted from natural nucleotides.

Figure 3:
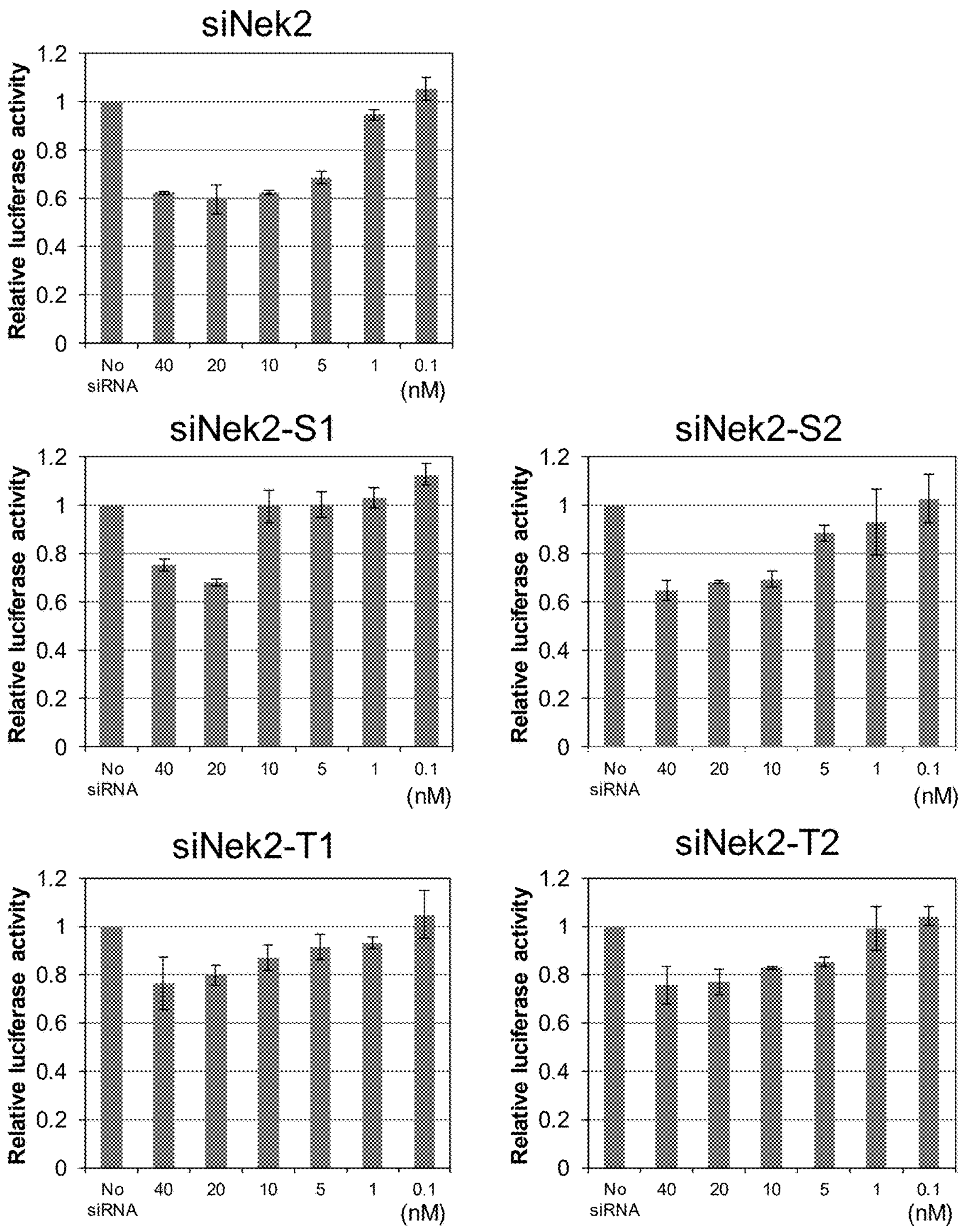
FIG. 3 shows the results of an evaluation of the off-target effects of the RNA interference agent prepared in the First Embodiment.

Next, the off-target effects of the passenger strand (sense strand) were confirmed by performing a luciferase assay as above using a plasmid prepared with a sequence complementary to the passenger strand. The results are shown in FIG. 3. As shown in FIG. 3, the off-target effects of the passenger strand were suppressed more than with natural siRNA. Of the agents, the RNA interference agent with the introduced TNA had a particularly strong ability to suppress off-target effects.

Figure 4:
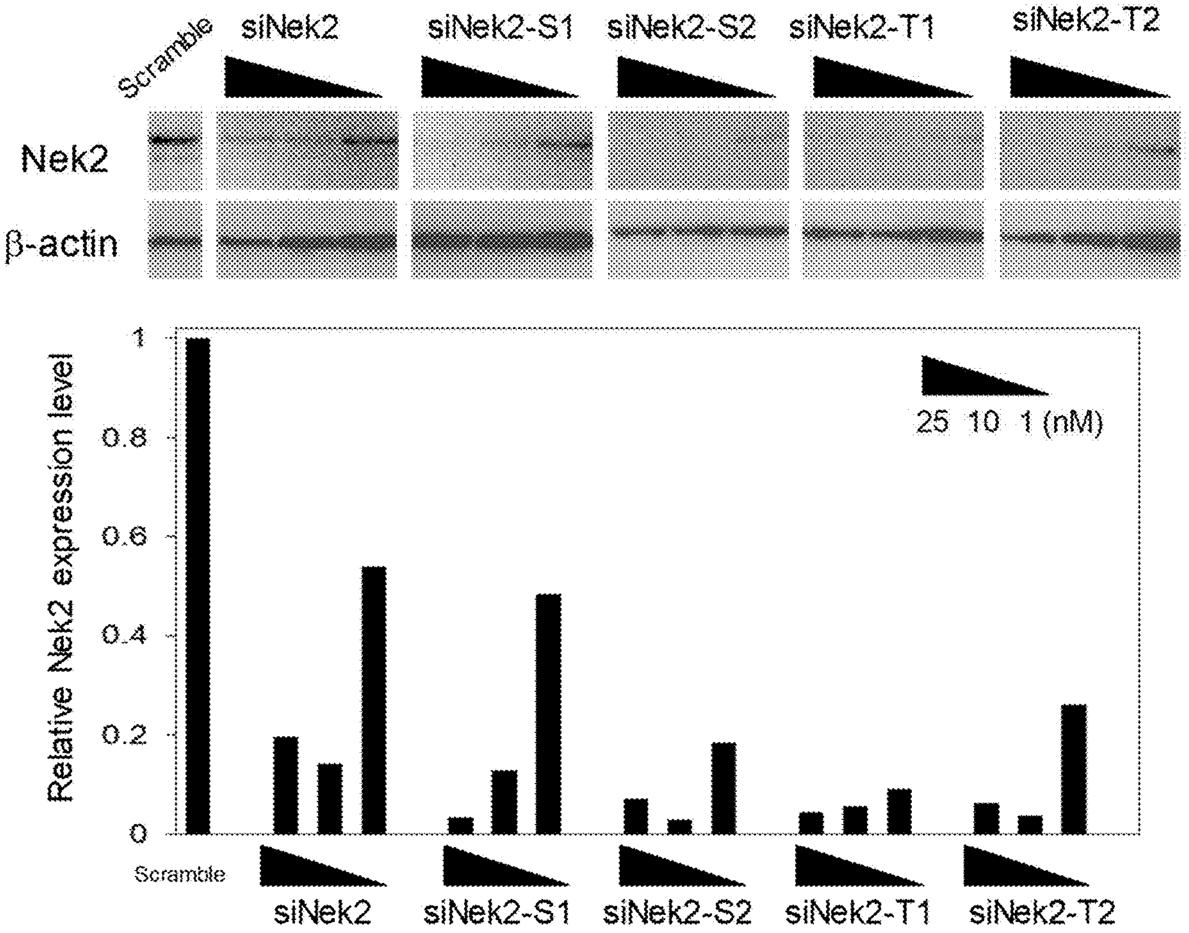
FIG. 4 shows the results of an evaluation (NeK2 protein Western blotting) of RNA interference by the RNA interference agent prepared in the First Embodiment.

Next, the prepared RNA interference agents were transfected with LIPOFECTAMINE™ 2000 (Nucleic acid delivery reagent containing lipid nanoparticles) into KLM1 cells, cells were collected after 48 hours, and expression of the endogenous Nek2 gene was analyzed by Western blotting using anti-NeK2 antibodies. The results are shown in FIG. 4. As shown in FIG. 4, the RNA interference agents having introduced SNA or TNA exhibited greater RNA interference ability than the natural siRNA.

Figure 5:
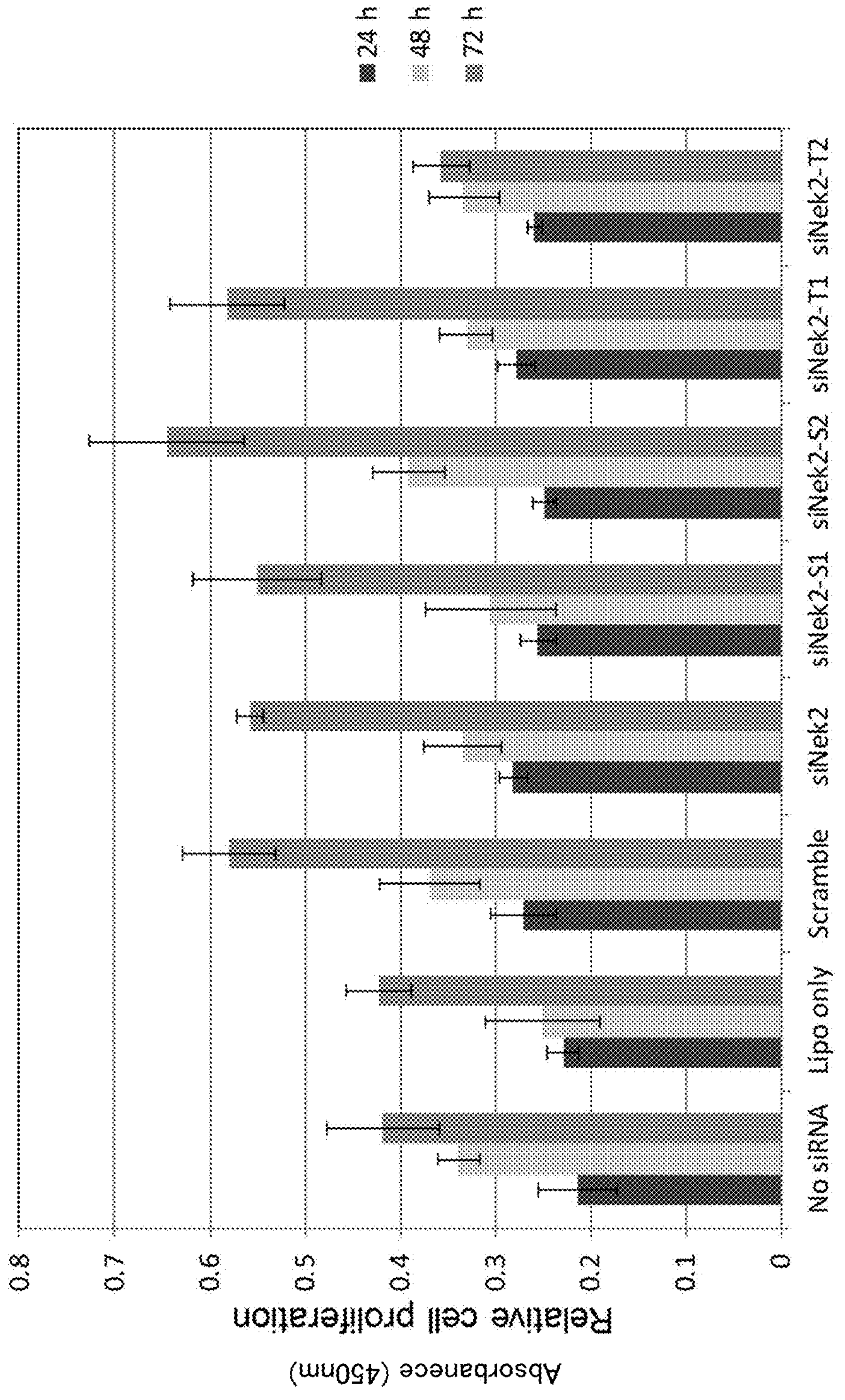
FIG. 5 shows the results of an evaluation by MTT assay of cell proliferation ability with the RNA interference agent prepared in the First Embodiment.

Since Nek2 is a protein associated with cell proliferation, moreover, the proliferation ability of cells treated with siRNA-Nek2 (10 nM) was evaluated to evaluate the effects of the RNA interference agent by MTT assay. That is, after transfection a WST-1 reagent was mixed with the cells for a specific period of time, after which absorbance was analyzed at 465 nm. The results are shown in FIG. 5. As shown in FIG. 5, the siNek2-T2 was the most effective in comparison with natural siRNA.

Figure 6:
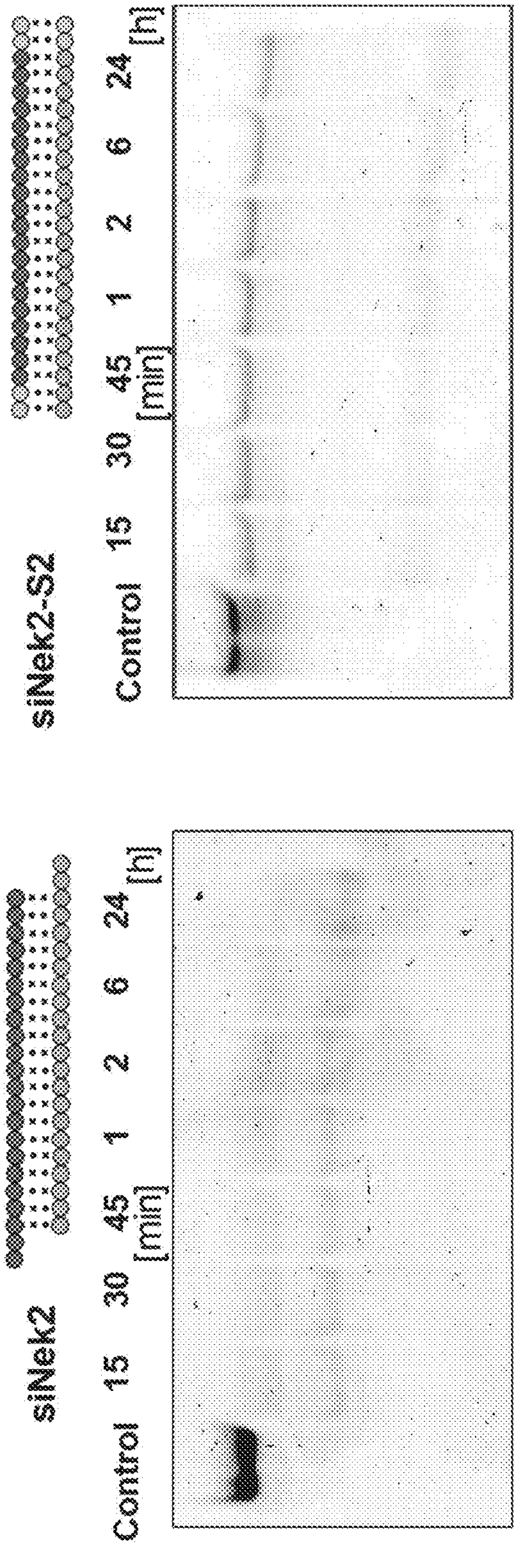
FIG. 6 shows the results of an evaluation of the enzyme resistance of the RNA interference agent prepared in the First Embodiment.

Furthermore, 1 μM of the RNA interference agent (siNek2-S2) having terminal introduced SNA was stored at 37° C. in 40% human serum, and the decomposition products were analyzed by 20% denatured PAGE. The results are shown in FIG. 6. As shown in FIG. 6, the RNA interference agent having the terminal introduced SNA had high enzyme resistance.

Second Embodiment (Preparation and Evaluation of Gapmer-Type Antisense Nucleic Acid)

SGLT2 (sodium glucose cotransporter 2, SLC5A2) is a glucose transporter that is expressed in the renal and proximal tubular cells and is a molecule responsible for reabsorption of filtered glucose in raw urine. Its expression is also known to be enhanced in diabetes. In this embodiment, a gapmer-type antisense nucleic acid was prepared targeting human SGLT2 gene mRNA, and its knockdown activity, urinary sugar excretion and side-effects (liver dysfunction and off-target effects (on SGLT1, SGLT5 and other transporters expressed in proximal renal tubules) and the like were evaluated.

In this embodiment, antisense nucleic acids were prepared with the following configurations. Specifically, the backbone part in capital letters was configured from deoxyribonucleotides attached by phosphorothioate bonds, and the backbone part in brackets was entirely substituted by phosphorothioate bonds with any of 2'MOE (2'-O-methoxyethylribonucleotide), SNA (formula (5)) and L-α-TNA (formula (6)) to prepare three kinds of antisense nucleic acids.

```
[C15]
                                  (SEQ ID NO: 11)
(G*G)*c*A*T*G*A*G*c*T*(T*C)
( ) = 2'MOE, SNA or L-aTNA
C = 5 Methyl dC
*= Phosphorothioation
```

[C16]

(5)

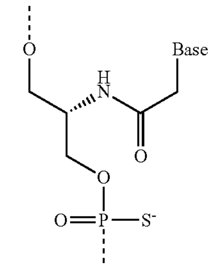

(6)

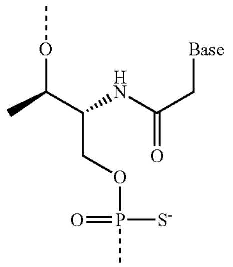

Figure 7:
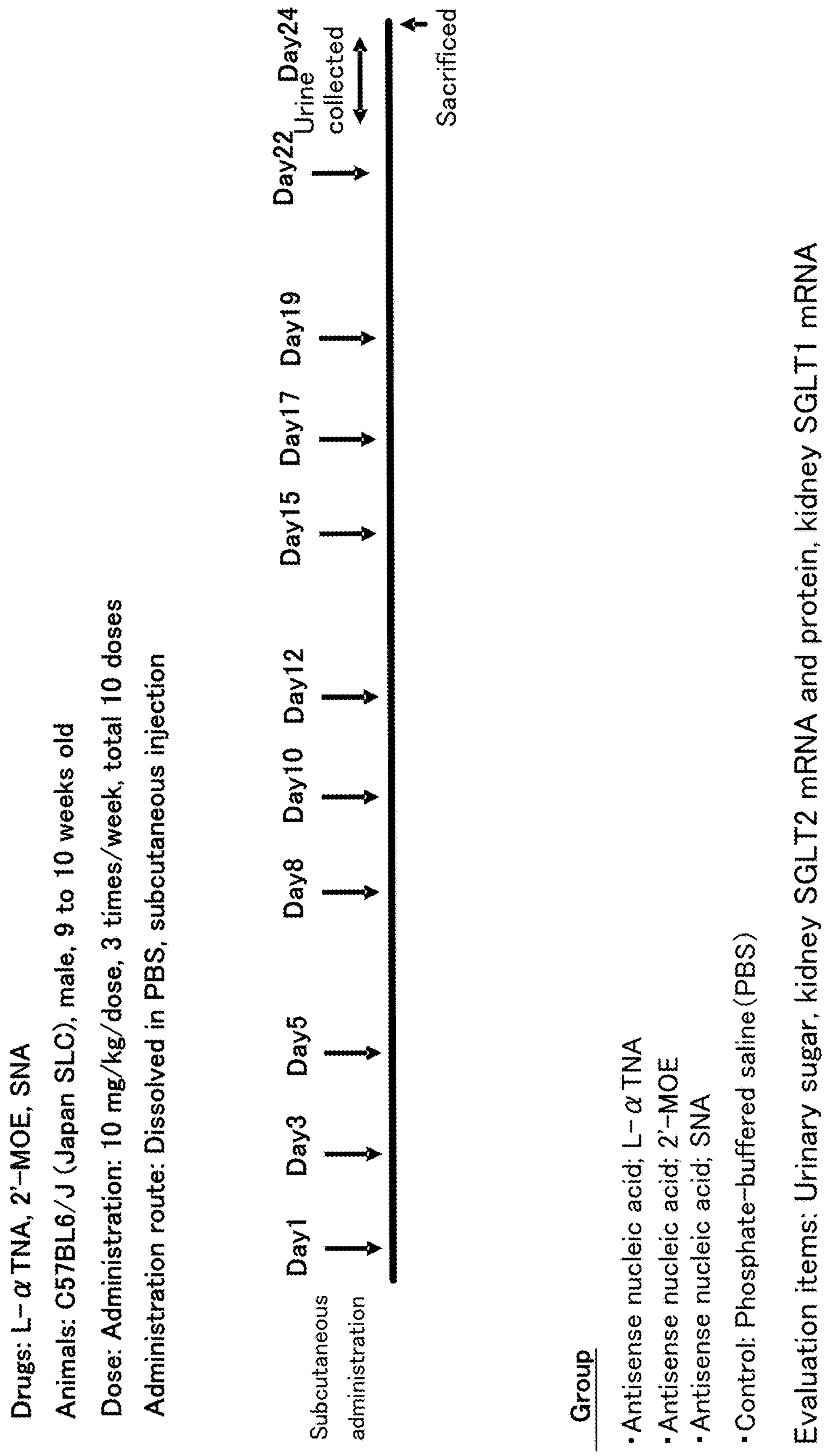
FIG. 7 shows an outline of protocols for mouse administration testing using the gapmer-type antisense nucleic acid prepared in the Second Embodiment.

Following the protocols shown in FIG. 7, mice (C57BL6/J, male, 9-10 weeks, purchased from Japan SLC, Inc.) were given a total of 10 subcutaneous (dorsal) injections of the prepared antisense nucleic acids at a rate of 3 times a week, 10 mg/kg per time. Subcutaneous injection was performed under inhalation anesthesia with isoflurane. Urine was collected the day after the final administration, and two days after the mice were sacrificed and kidneys, livers and serum were collected.

Figure 8:
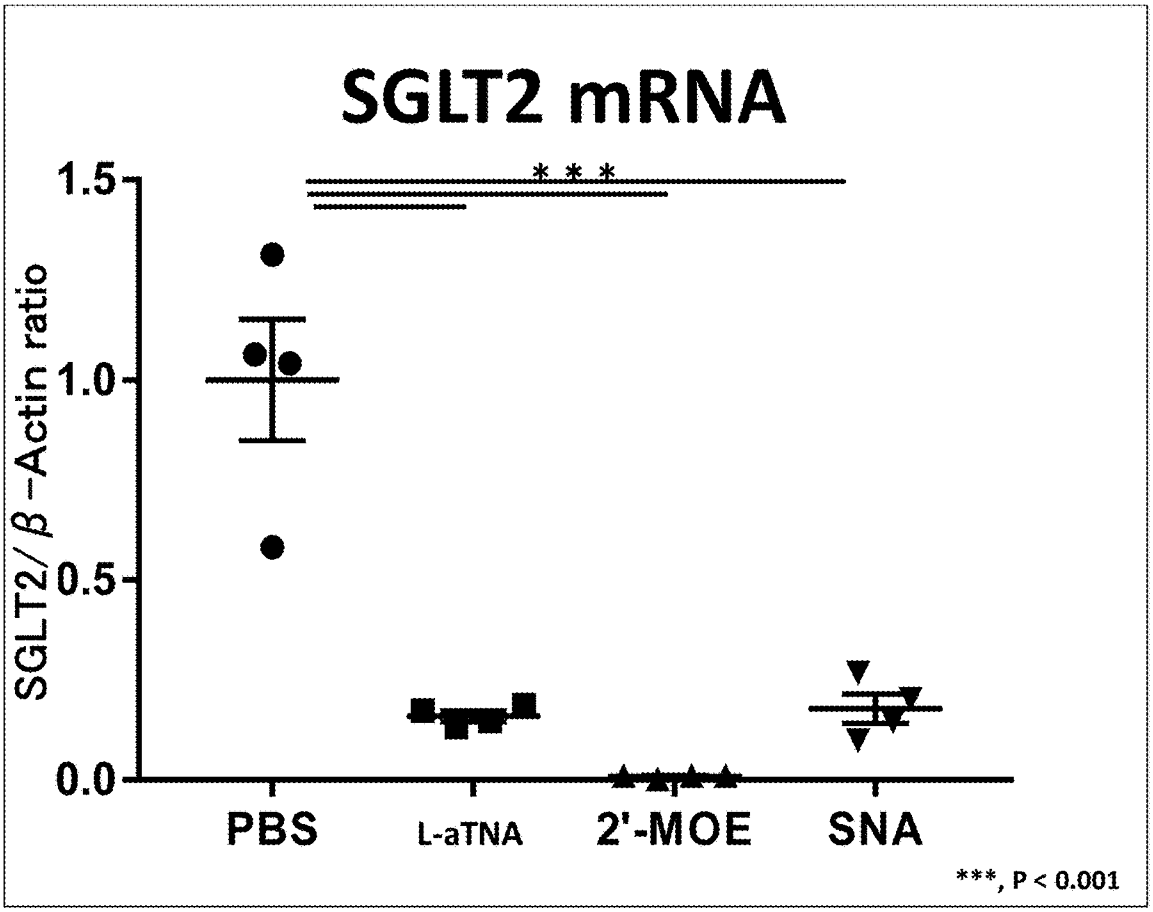
FIG. 8 shows the results of an evaluation of SGLT2 knockdown activity (amount of mRNA) with the gapmer-type antisense nucleic acid prepared in the Second Embodiment.
Figure 9:
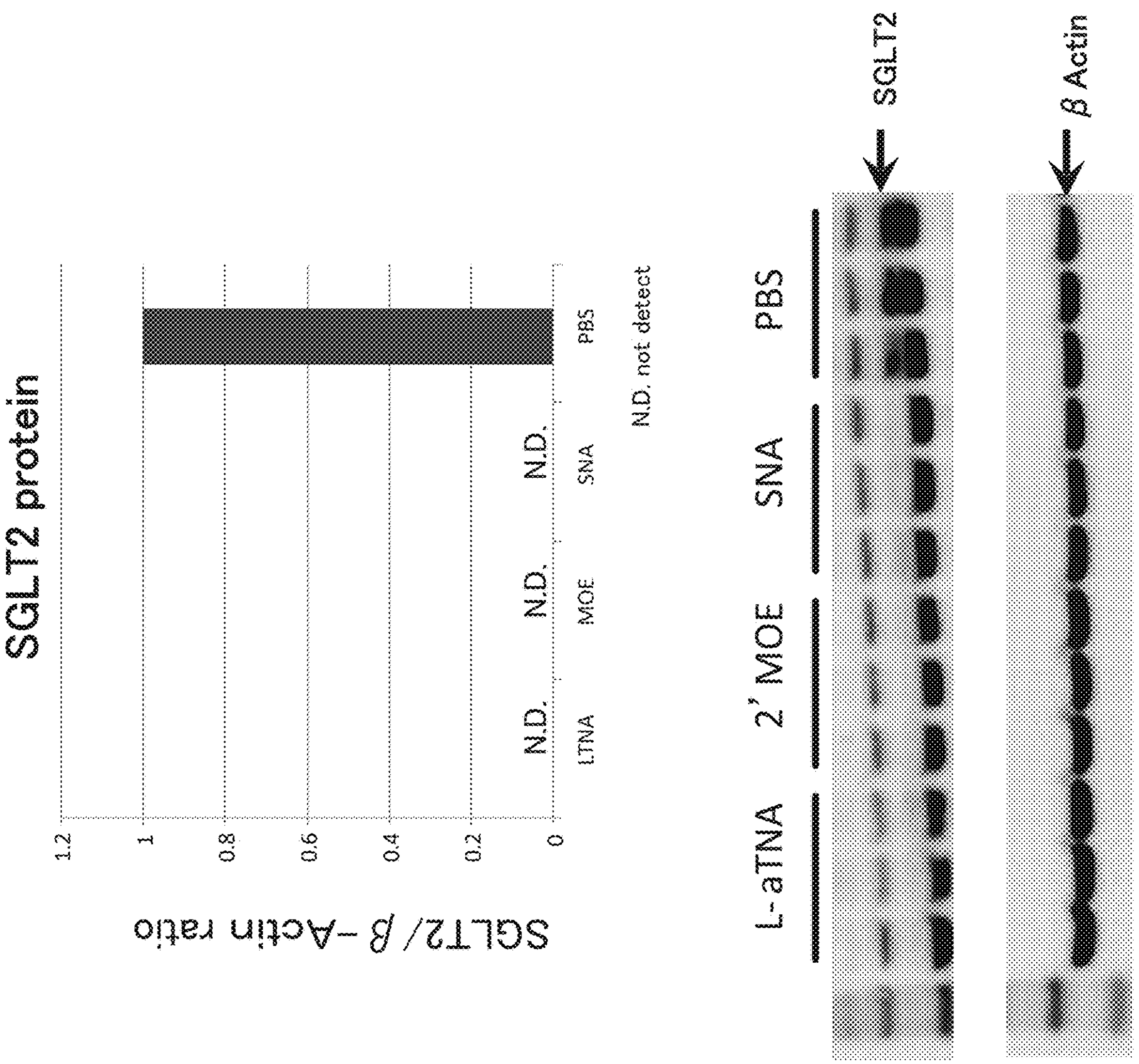
FIG. 9 shows the results of an evaluation of SGLT2 knockdown activity (amount of protein) with the gapmer-type antisense nucleic acid prepared in the Second Embodiment.
Figure 10:
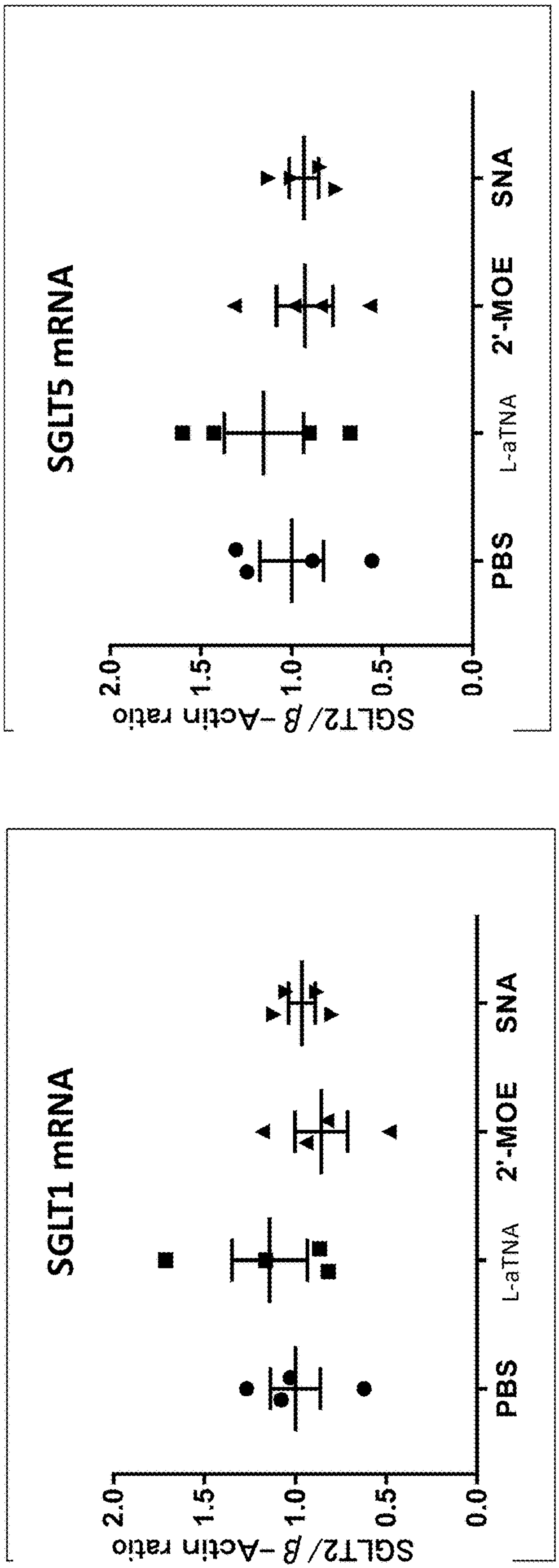
FIG. 10 shows the results of an evaluation of the off-target effects of the gapmer-type antisense nucleic acid prepared in the Second Embodiment.

The amount of SGLT2 mRNA and the amount of the expressed protein in the collected mouse kidneys were measured. The results are shown in FIG. 8 and FIG. 9. As shown in FIG. 8 and FIG. 9, subcutaneous administration of antisense nucleic acids having introduced SNA and L-aTNA dramatically reduced the level of SGLT2 mRNA and the amount of the SGLT2 protein in kidneys. The SGLT1 and SGLT5 mRNA levels were also measured at the same time. The results are shown in FIG. 10. It was confirmed that none of the antisense nucleic acids reduced the mRNA levels of these genes. That is, no non-specific (independent of nucleotide sequence) expression suppression effects (off-target effects) were observed with respect to molecules other than the target SGLT2 with the antisense nucleic acids used here.

Urinary sugar excretion was evaluated using the collected urine. The results are shown in FIG. 11. As shown in FIG. 11, no urinary sugar was observed in the PBS administration group, but urinary sugar excretion was observed in all of the antisense nucleic acid administration groups. These results show that the effects of SGLT2 were greatly weakened, and the glucose reabsorption capacity of the renal tubules was reduced.

Third Embodiment (Preparation and Evaluation of Molecular Beacon Probe)

In this embodiment, using 30-mers containing T790 of the EGFR gene (wild type and mutation (single nucleotide substitution)) as the target RNA, corresponding molecular beacon probes were designed with recognition sites ranging in length from 14-mer to 18-mer for the target RNA, with the entire backbone of the probe strand including the other stem-forming region consisting of SNA (formula (1)), and with a fluorescent dye and a quenching dye introduced at both ends (Table 2). The fluorescent dye and quenching dye are perylene and anthraquinone in the molecular beacons for detecting the wild type, and Cy3 and nitromethyl red in the molecular beacons (T790M) for detecting the mutation.

X

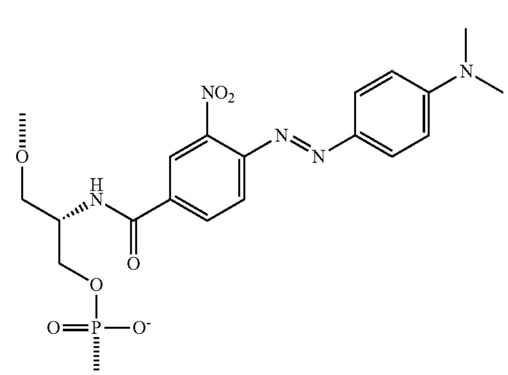

Y

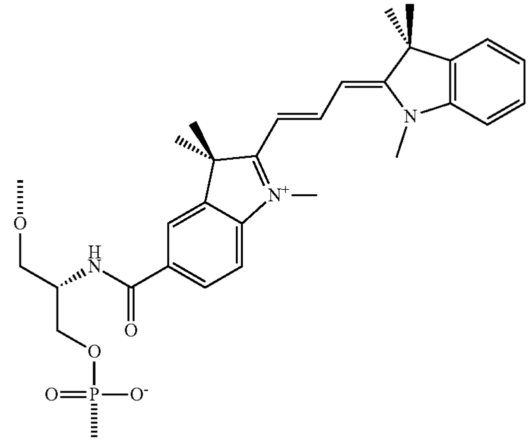

Q

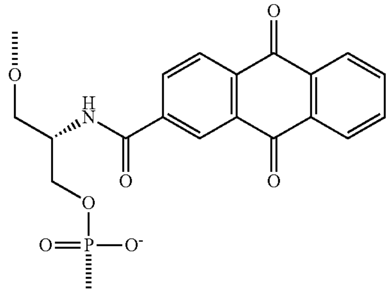

TABLE 2

| | Name | Sequences | Recognition site | Stem | SEQ NO: |
|---|---|---|---|---|---|
| Target RNA | T790M mutation | 5'-CCGUGCAGCUCAUCAUGCAGCUCAUGCCCU-3' | | | 12 |
| | T790M wild type | 5'-CCGUGCAGCUCAUCACGCAGCUCAUGCCCU-3' | | | 13 |
| SNA-MB for wild type | 27mer wild | (S)-**QQ**TGCAGC-GCTGCGTGATGA-GCTGCA**F**-(R) | 18 mer | 6 mer | 14 |
| | 26mer wild | (S)-**QQ**TGCAG-GCTGCGTGATGAG-CTGCA**F**-(R) | 18 mer | 5 mer | 15 |
| | 24mer wild | (S)-**QQ**CAGCT-GCTGCGTGATG-AGCTG**F**-(R) | 16 mer | 5 mer | 16 |
| | 22mer wild | (S)-**QQ**GCTCA-GCTGCGTGA-TGAGC**F**-(R) | 14 mer | 5 mer | 17 |
| SNA-MB for mutation | 27mer mutation | (S)-**XX**TGCAGC-GCTGCATGATGA-GCTGCA**Y**-(R) | 18 mer | 6 mer | 18 |
| | 26mer mutation | (S)-**XX**TGCAG-GCTGCATGATGAG-CTGCA**Y**-(R) | 18 mer | 5 mer | 19 |
| | 24mer mutation | (S)-**XX**CAGCT-GCTGCATGATG-AGCTG**Y**-(R) | 16 mer | 5 mer | 20 |

X = Nitro Methyl Red,
Y = Cy3,
Q = Anthraquinone,
F = Perylene

-continued

F

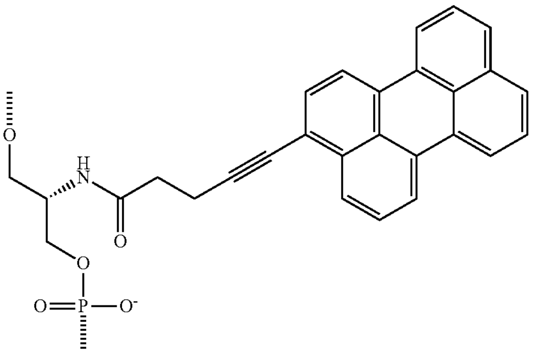

Using these molecular beacon probes for detecting the wild type and mutation, 0.2 μM of each probe and 0.2 μM of the target RNA at 37° C. (mRNA of wild type or mutant EGFR gene) were incubated for 5 minutes in 100 mM NaCl, 10 mM phosphoric acid buffer (pH 7.0) at various temperatures with an excitation wavelength of 440 nm and an emission wavelength of 472 nm (both perylene) or an excitation wavelength of 546 nm and an emission wavelength of 565 nm (both Cy3), and fluorescent intensity was measured. To calculate the S/B ratio, the fluorescent intensity was also measured using only the probe without the target RNA. The fluorescent intensities at 37° C. are shown in the following table.

TABLE 3

| | MB only | +T790M wild | +T790M mutation | S/B (full-match/ MB only) | Discrimination (full-match/ mismatch) |
|---|---|---|---|---|---|
| 27mer wild | 14.5 | 424 | 46.5 | 29.2 | 9.12 |
| 26mer wild | 11.1 | 468 | 75.4 | 42.2 | 6.21 |
| 24mer wild | 8.0 | 312 | 29.6 | 39.0 | 10.5 |
| 22mer wild | 1.6 | 97.9 | 4.68 | 61.2 | 20.9 |
| 27mer mutation | 6.59 | 43.5 | 114 | 17.3 | 2.62 |
| 26mer mutation | 3.62 | 53.3 | 218 | 60.2 | 4.09 |
| 24mer mutation | 1.8 | 27.8 | 90.6 | 50.3 | 3.26 |

As shown in the above table, both wild-type and mutant RNA could be detected as target RNA with all of the molecular beacon probes, and the S/B was at least 15 with all the probes, indicating that the wild type and mutant can be distinguished.

Fourth Embodiment (Preparation of High Sensitivity Molecular Beacon Probe)

In this embodiment, as shown in FIG. 12, miR21 was used as the target RNA, and a molecular beacon probe was prepared having stem-forming regions disposed on both sides of the hybridizing region that hybridizes with the target RNA, having 2,6-diaminopurine substituted at adenine sites near the stem-forming region, and having Cy3 as a fluorescent dye and methyl red as a quenching dye introduced into the nucleotides of the probe strand. SNA (formula (1)) was adopted for the entire backbone part.

Figure 13:
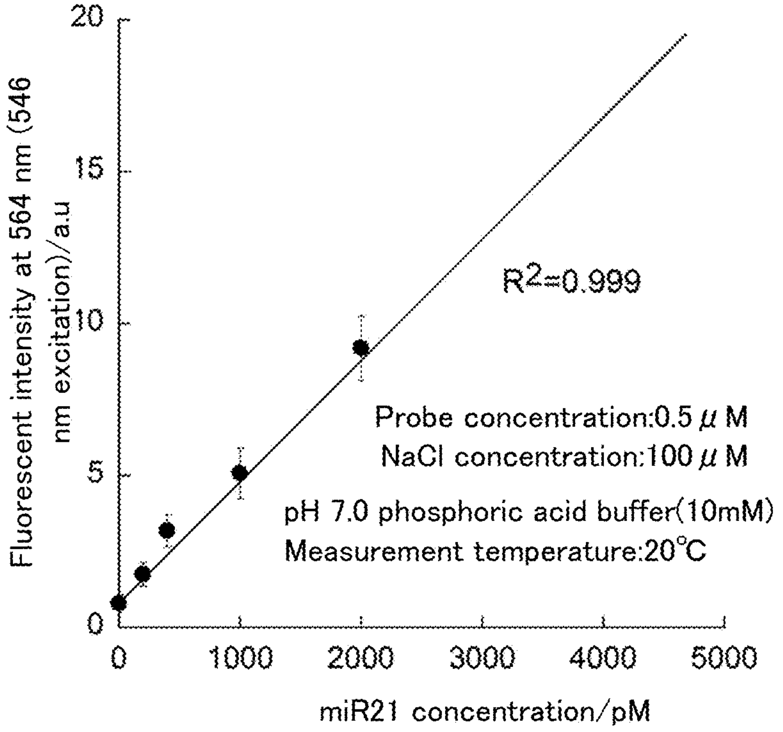
FIG. 13 shows the amount of target RNA detected with the molecular beacon probe prepared in the Fourth Embodiment.

Using 1 μM of this molecular beacon probe and 2 μM of the target RNA at 20° C. in 100 mM NaCl, 10 mM phosphoric acid buffer (pH 7.0), the fluorescent spectrum was measured at an excitation wavelength of 546 nm and an emission wavelength of 565 nm as the temperature was lowered from 80° C. at a rate of 1° C./minute. Fluorescent intensity was also measured at different target RNA concentrations under the same conditions except that the probe concentration was 0.5 μM, the target RNA concentration ranged from 0 to 2,000 μM, and the emission wavelength was 564 nm. The results are shown in FIG. 12 and FIG. 13.

As shown in FIG. 12, The S (signal)/B (background) ratio was 205×, which is more than 100×. As shown in FIG. 13, the detection limit for the target RNA was 200 μM. This shows that excellent detection performance can be achieved with a molecular beacon probe having an SNA backbone and 2,6-diaminopurine near the stem-forming region. When the S/B ratio and detection limit were confirmed similarly with respect to a molecular beacon probe prepared in the same way without substituting 2,6-diaminopurine, the results were favorable, showing lower values than with the molecular beacon containing 2,6-diaminopurine.

Fifth Embodiment (Preparation and Evaluation of Gapmer-Type Antisense Nucleic Acids 2)

Gapmer-type antisense nucleic acids targeting mRNA of the human SGLT2 gene were prepared as in the Second Embodiment, and the knockdown activity, urinary sugar excretion and side-effects (liver dysfunction) were evaluated.

In this embodiment, antisense nucleic acids were prepared with the following configurations. Specifically, 4 kinds of antisense nucleic acids were prepared with the backbone part in capital letters configured from deoxyribonucleotides attached by phosphorothioate bonds, and with the backbone part in brackets entirely substituted by phosphorothioate bonds with any of 2'MOE (2'-O-methoxyethylribonucleotide), SNA and 5-methyl dC.

[C17]

```
SNA2, MOE2 x
                                   SEQ ID NO: 11)
(G)*G*c*A*T*G*A*G*c*T*T*(c)

SNA PS, MOE PS
                                   SEQ ID NO: 11
(G*G)c*A*T*G*A*G*c*T(T*c)
( ) = SNA, 2'MOE
c = 5 Methyl dC
*= Phosphorothioation
```

For these antisense nucleic acids, following the protocols shown in FIG. 14, mice (C57BL6/J, male, 9-10 weeks, purchased from Japan SLC, Inc.) were given a total of 10 subcutaneous injections of the prepared antisense nucleic acid at a rate of 3 times a week, 10 mg/kg per injection. Urine was collected the day after the final administration, and two days after the mice were sacrificed and blood and kidney tissue were collected.

Figure 15:
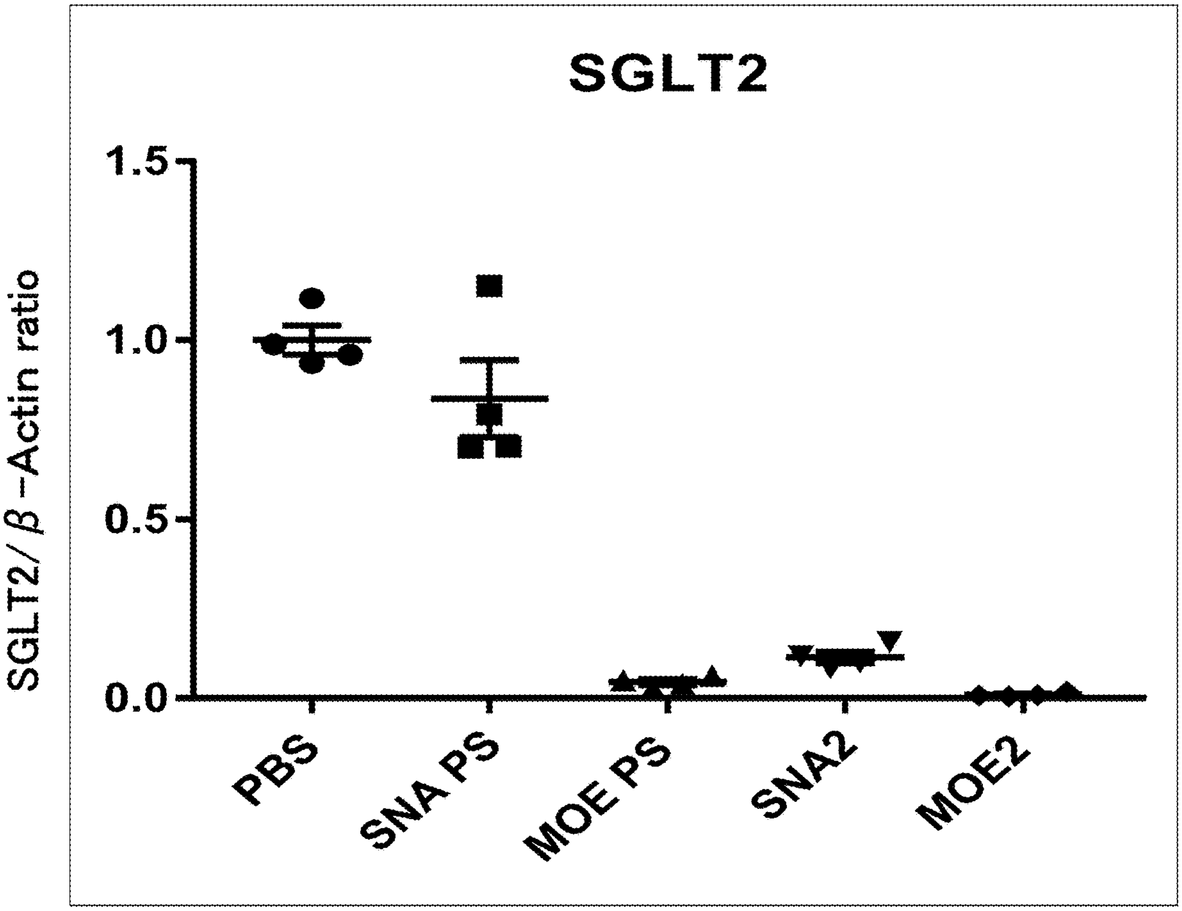
FIG. 15 shows the results of an evaluation of SGLT2 knockdown activity (amount of mRNA) with the gapmer-type antisense nucleic acid prepared in the Fifth Embodiment.
Figure 16:
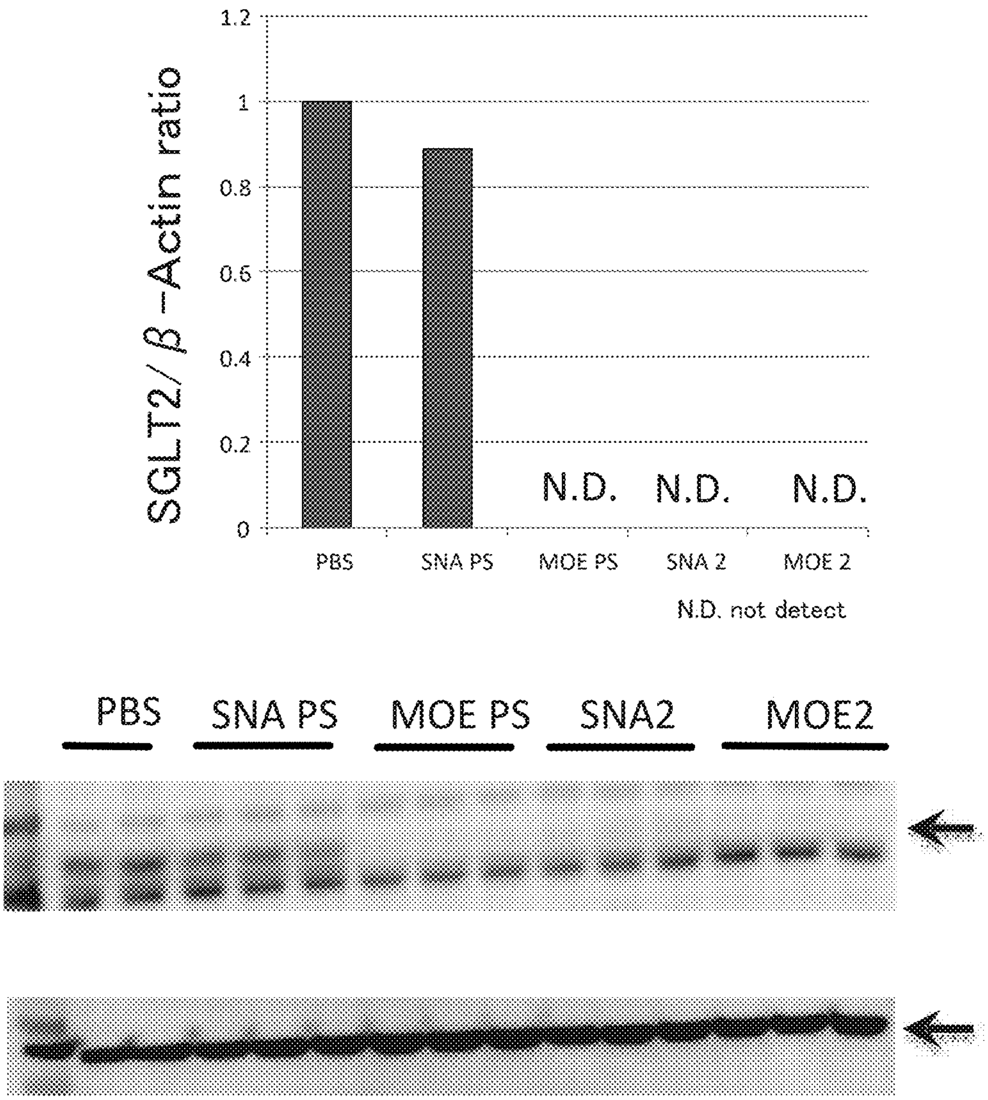
FIG. 16 shows the results of an evaluation of SGLT2 knockdown activity (amount of protein) with the gapmer-type antisense nucleic acid prepared in the Fifth Embodiment.

The amount of SGLT2 mRNA and the amount of the expressed protein in the collected mouse kidneys were measured as in the Second Embodiment, with the results shown in FIG. 15 and FIG. 16. As shown in FIG. 15 and FIG. 16, subcutaneous administration of an antisense nucleic acid having only one SNA introduced at both ends reduced the level of SGLT2 mRNA and the amount of the SGLT2 protein in the kidneys in all cases. With a SNA antisense nucleic acid with a phosphate diester bond as the second phosphorothioate from both ends, on the other hand, the level of SGLT2 mRNA in the kidneys fell by only about 15%, and the amount of the SGLT2 protein fell by only about 10%.

Figure 17:
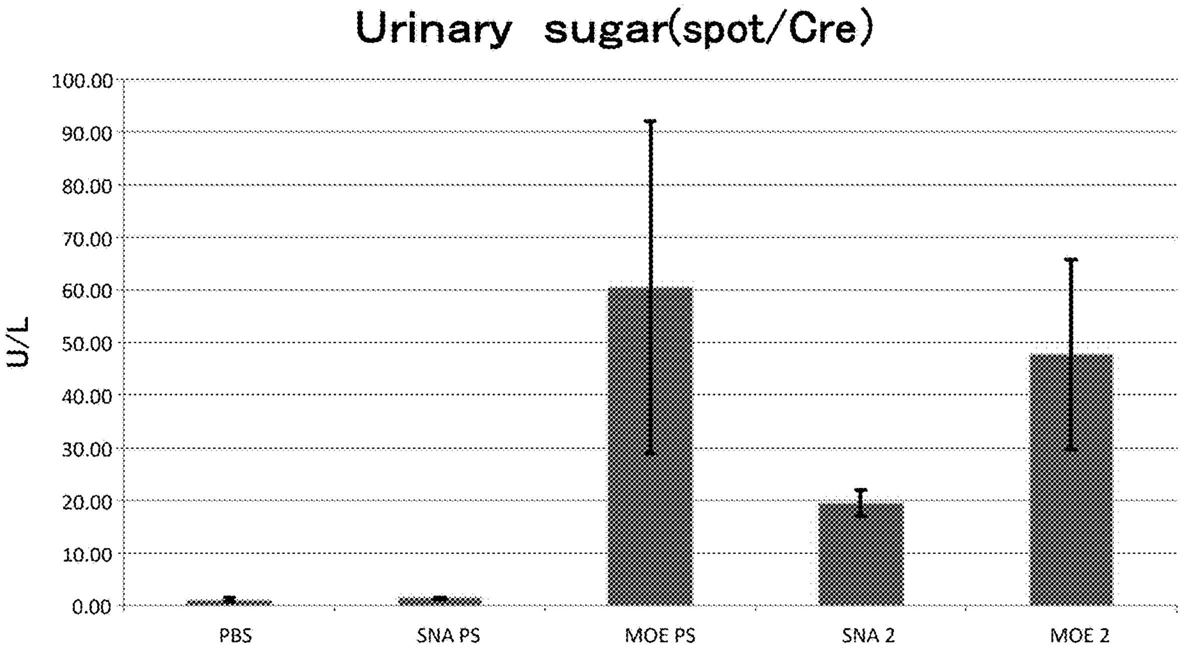
FIG. 17 shows the results of an evaluation of increased urinary sugar excretion with the gapmer-type antisense nucleic acid prepared in the Fifth Embodiment.
Figure 18:
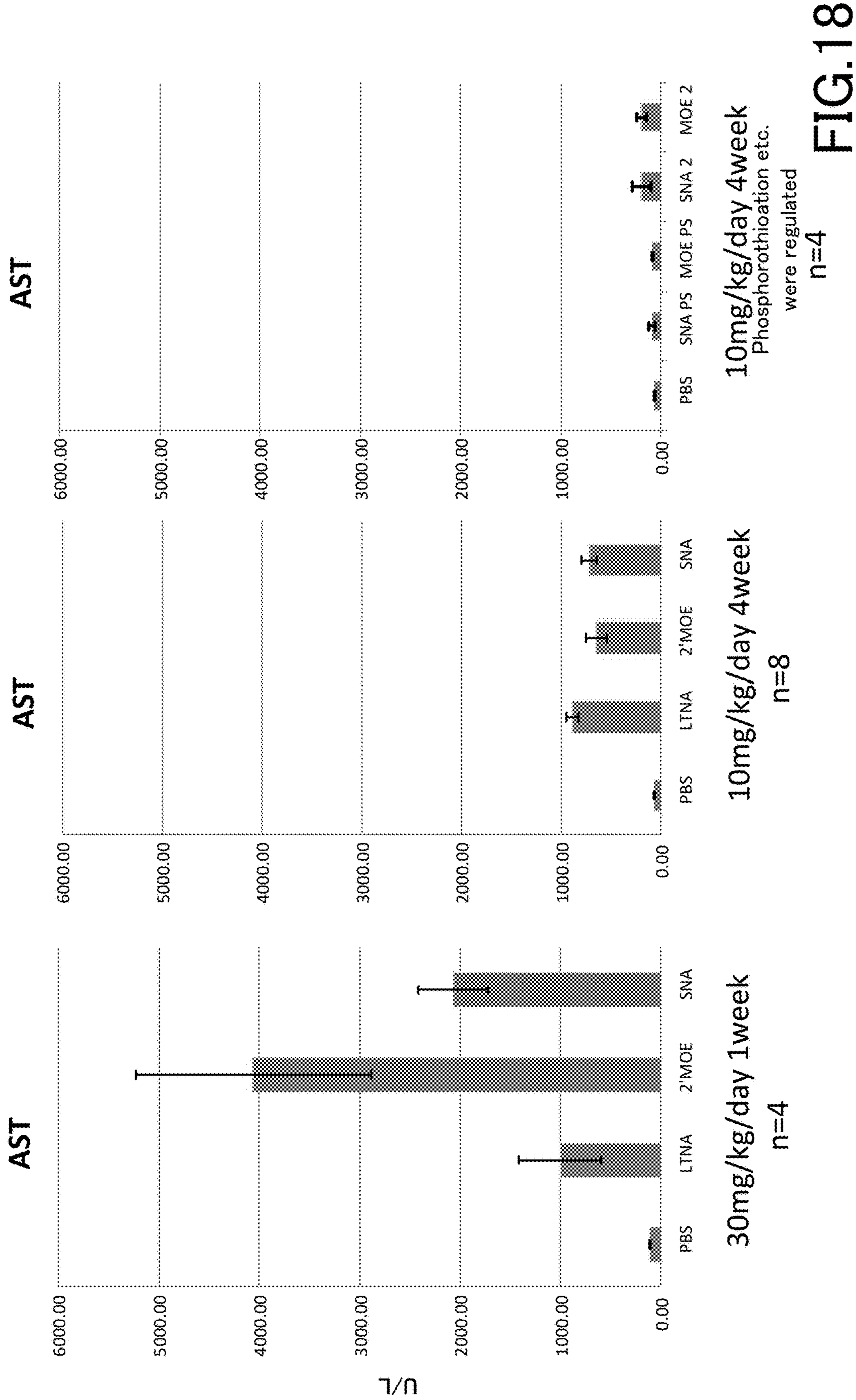
FIG. 18 shows the results of an evaluation of liver side-effects (AST) with the gapmer-type antisense nucleic acid prepared in the Fifth Embodiment.

FIG. 17 shows results of an evaluation of urinary sugar excretion using urine collected as in the Second Embodiment. As shown in FIG. 17, no urinary sugar was observed in the PBS administration group, but urinary sugar excretion was observed in all of the antisense nucleic acid administration groups except in the case of the SNA gapmer having a phosphate diester bond as the second phosphorothioate from both ends, showing that the effects of SGLT2 were greatly weakened, and the glucose reabsorption capacity of the renal tubules was reduced.

Figure 19:
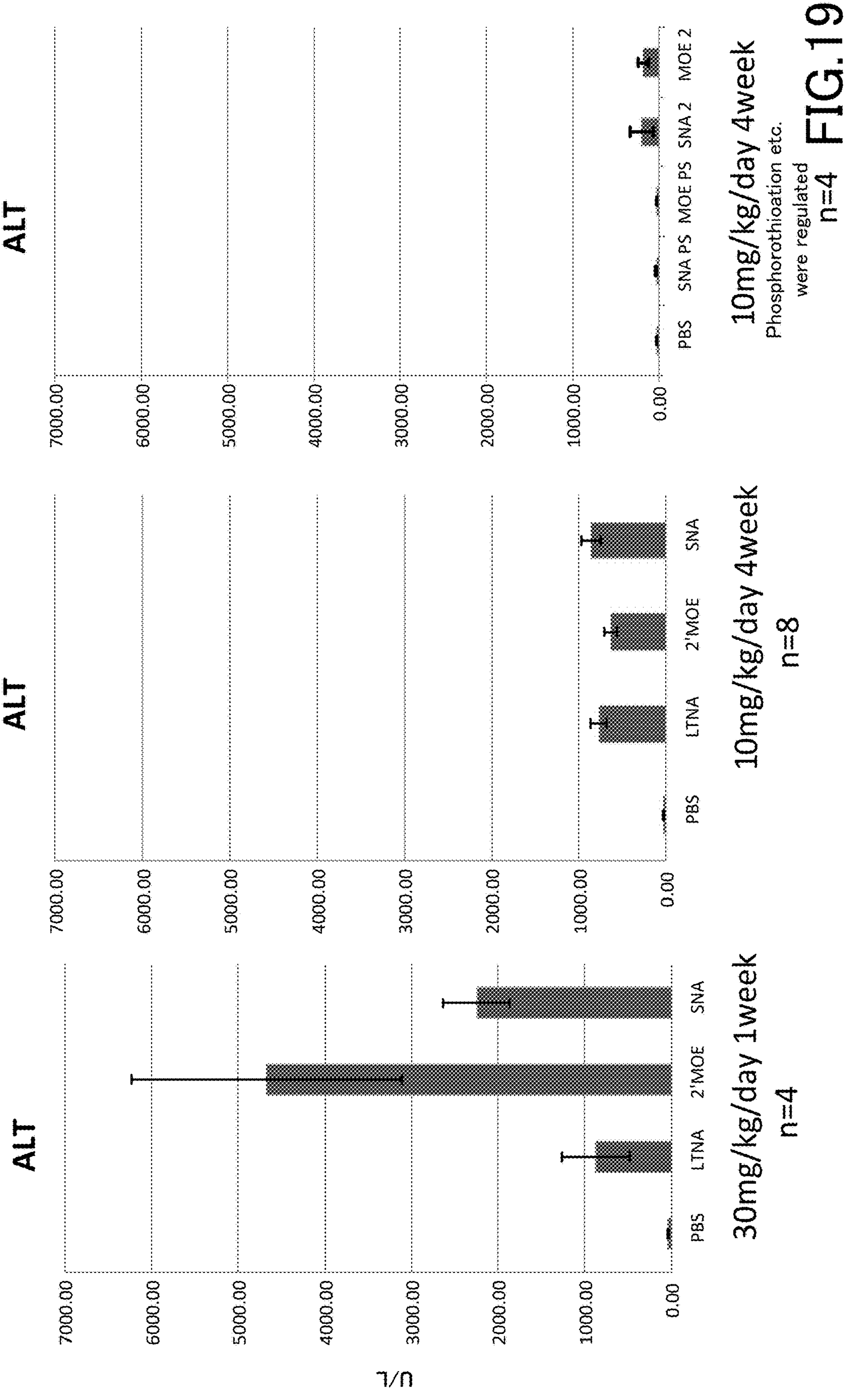
FIG. 19 shows the results of an evaluation of liver side-effects (ALT) with the gapmer-type antisense nucleic acid prepared in the Fifth Embodiment.
Figure 20:
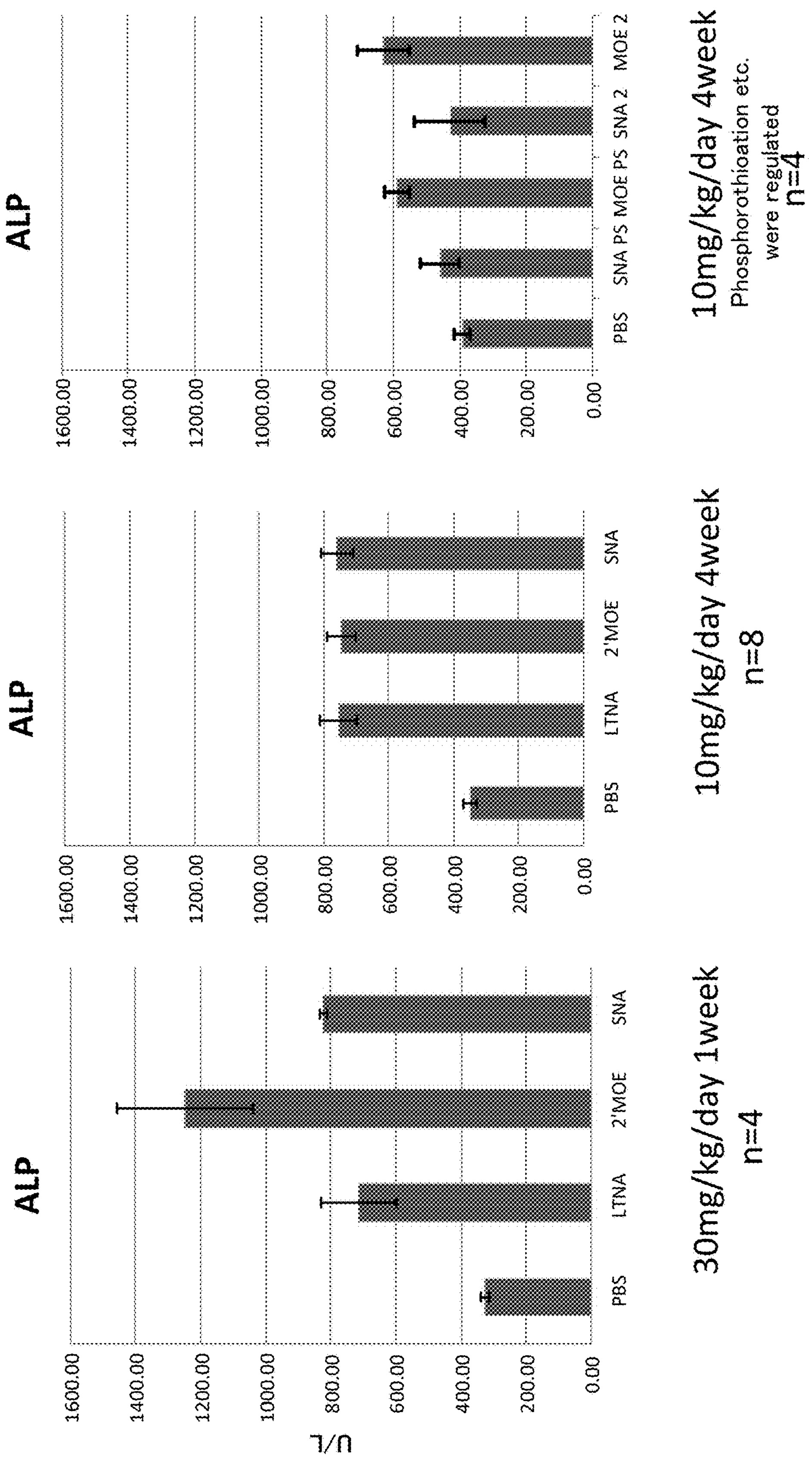
FIG. 20 shows the results of an evaluation of liver side-effects (ALP) with the gapmer-type antisense nucleic acid prepared in the Fifth Embodiment.

AST, ALT and ALP were also evaluated using the collected blood. The results are shown in FIG. 16, FIG. 19 and FIG. 20. As shown in FIG. 19 and FIG. 20, the side-effects on liver function were weaker in all cases in comparison with the results of the Second Embodiment.

Sixth Embodiment (Preparation and Evaluation of Gapmer-Type Antisense Nucleic Acids 3)

Gapmer-type antisense nucleic acids targeting mRNA of the SGLT2 gene were prepared as in the Second Embodiment, and their knockdown activity and long-lasting effects were evaluated. In this embodiment, antisense nucleic acids were prepared with the following configurations. Specifically, 3 kinds of antisense nucleic acids were prepared with each backbone part in capital letters configured from deoxyribonucleotides attached by phosphorothioate bonds, and with the backbone part in brackets entirely substituted with SNA by phosphorothioate bonds.

| | |
|---|---|
| DNA: | G*g*c*A*T*G*A*G*c*T*T*C (SEQ ID NO: 11) |
| Capital letters: | DNA |
| c | 5-methyl dC |
| * | Phosphorothioate |
| SNA2: | (G)*G*c*A*T*G*A*G*c*T*T*(C) (SEQ ID NO: 11) |
| ( ) | SNA |
| c | 5-methyl dC |
| * | Phosphorothioate |
| SNA4: | (G*G)*c*A*T*G*A*G*c*T*(T*C) (SEQ ID NO: 11) |
| ( ) | SNA |

-continued

| | |
|---|---|
| c | 5-methyl dC |
| * | Phosphorothioate |

Figure 21:
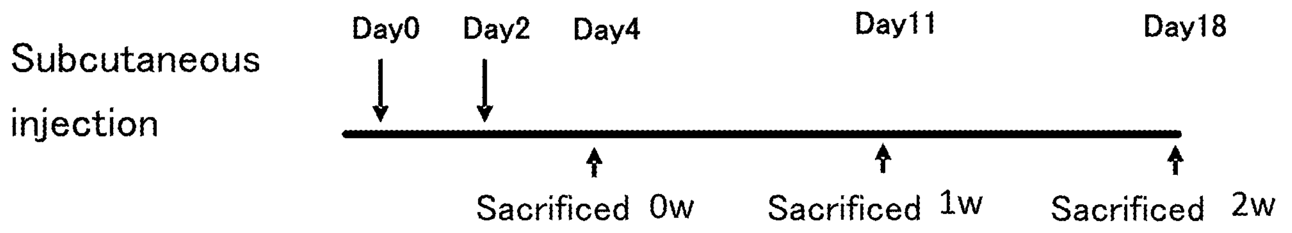
FIG. 21 shows an outline of protocols for mouse administration testing using the gapmer-type antisense nucleic acid prepared in the Sixth Embodiment.

For these antisense nucleic acids, following the protocols shown in FIG. 21, each of the prepared antisense nucleic acids was administered to mice (C57BL6/J, male, 9-10 weeks, purchased from Japan SLC, Inc.) twice by subcutaneous injection of 10 mg/Kg on day 0. 2 days, 9 days and 16 days after the final injection the mice were sacrifice, and kidney tissue was collected. The amount of SGLT2 mRNA in the collected mouse kidneys was measured as in the Second Embodiment, with the results shown in FIG. 22, FIG. 23 and FIG. 24.

Figure 22:
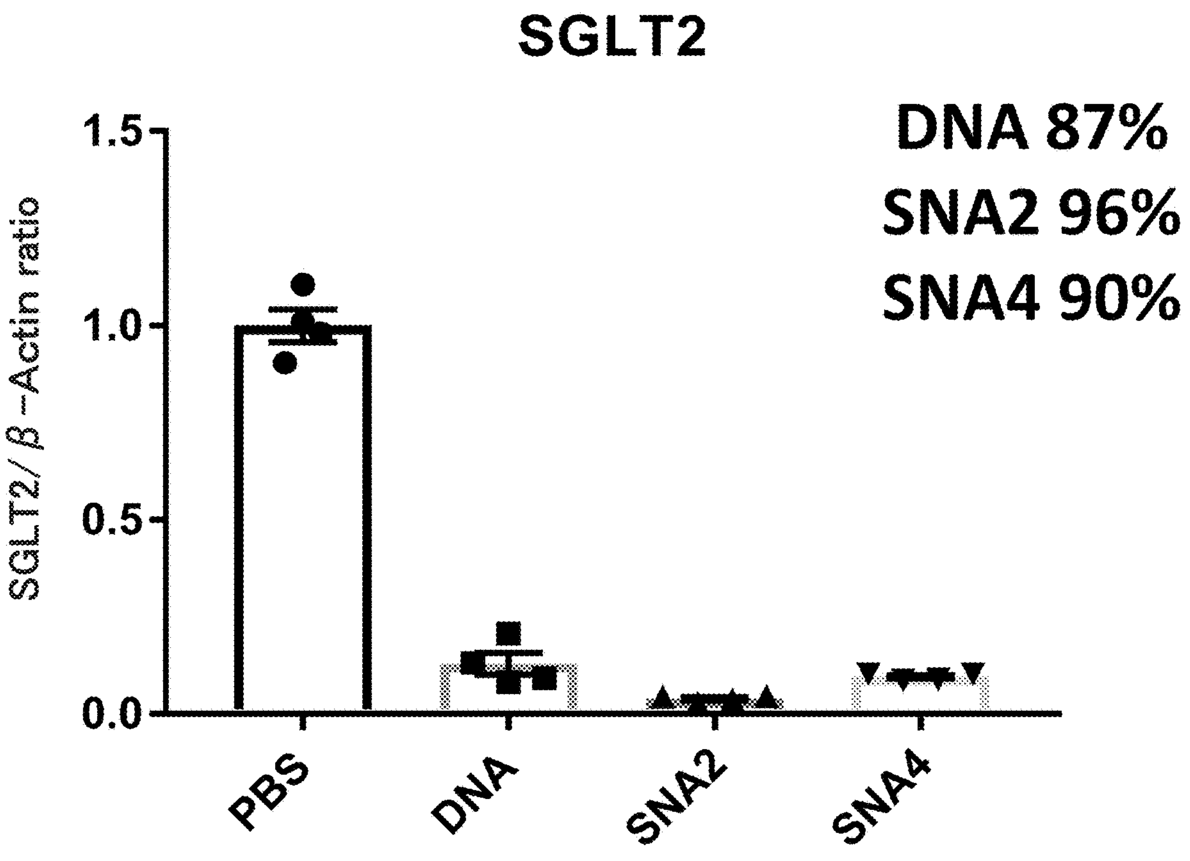
FIG. 22 shows the results of an evaluation of the amount of SGLT2 mRNA (0 W) in kidneys with the gapmer-type antisense nucleic acid prepared in the Sixth Embodiment.
Figure 23:
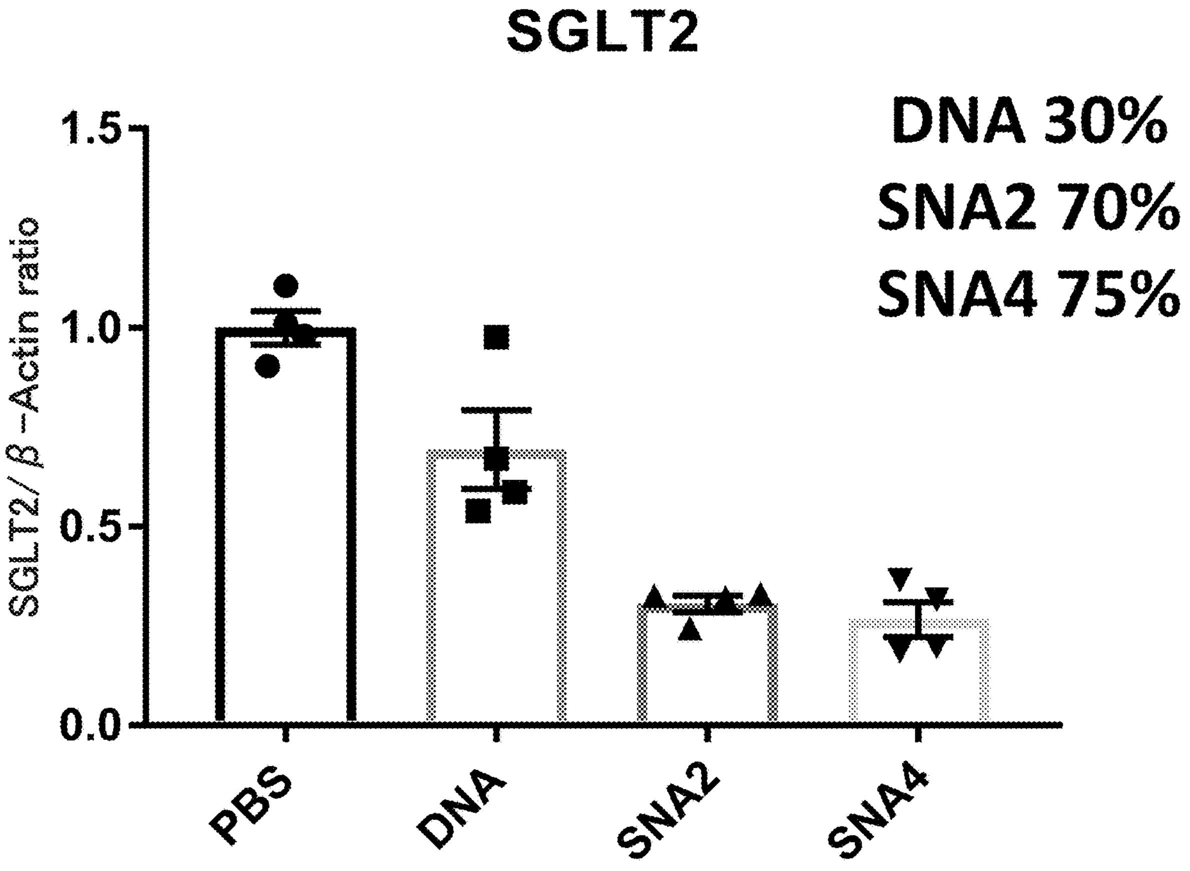
FIG. 23 shows the results of an evaluation of the amount of SGLT2 mRNA (1 W) in kidneys with the gapmer-type antisense nucleic acid prepared in the Sixth Embodiment.
Figure 24:
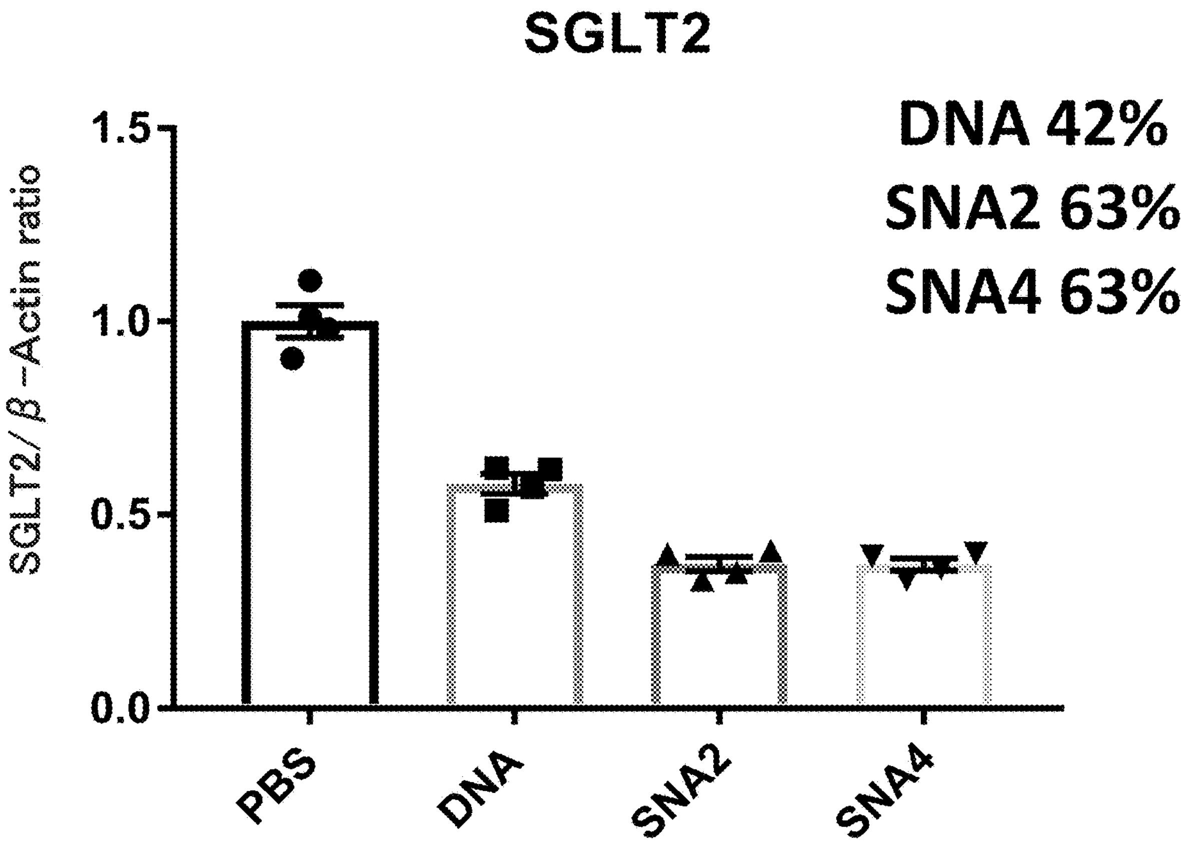
FIG. 24 shows the results of an evaluation of the amount of SGLT2 mRNA (2 W) in kidneys with the gapmer-type antisense nucleic acid prepared in the Sixth Embodiment.

As shown in FIG. 22, 2 days after the final administration subcutaneous administration of the antisense nucleic acids having one or two SNAs introduced on both sides and the antisense nucleic acid composed of DNA had reduced SGLT2 mRNA levels in kidneys in all cases. As shown in FIG. 23, 9 days after the final administration subcutaneous administration of the antisense nucleic acids having one or two SNAs introduced on both sides had reduced SGLT2 mRNA levels by 70% and 75%, respectively, while subcutaneous administration of the antisense nucleic acid composed of DNA had reduced it by only 30%. Furthermore, as shown in FIG. 24, 16 days after the final administration subcutaneous administration of the antisense nucleic acids having one or two SNAs introduced on both sides had reduced SGLT2 mRNA levels by 63% in both cases, while subcutaneous administration of the antisense nucleic acid composed on DNA had reduced it by only 42%.

These results show that in comparison with subcutaneous administration of an antisense nucleic acid composed of DNA, subcutaneous administration of an antisense nucleic acid having one or two SNAs introduced on both sides continuously weakens the action of SGLT2. These results show that such an antisense nucleic acid is an effective drug in terms of nuclease resistance and knockdown effects.

SEQUENCE LISTING FREE TEXT

SEQ ID NOS: 1 to 10: siRNA
SEQ ID NO: 11: Gapmer Type Antisense Nucleic Acid
SEQ ID NOS: 14 to 21: Molecular Beacon Probe
Sequence Listing

The invention claimed is:

1. An RNA interference agent comprising a passenger strand and a guide strand for a target RNA, wherein both ends of double-stranded RNA formed by pairing of the passenger strand and the guide strand constitute blunt ends, and wherein the passenger strand comprises two units represented by formula (2) at each of 5' end side and 3' end side and the guide strand comprises two units represented by formula (2) at the 3' end side, (2)

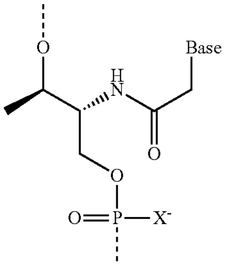

where X represents an oxygen atom or sulfur atom.

2. The RNA interference agent according to claim 1, wherein the target RNA is mRNA of NeK2 gene.

3. The RNA interference agent according to claim 2, wherein the passenger strand has the base sequence represented by SEQ ID NO:9, and the guide strand has the base sequence represented by SEQ ID NO:10.

4. A method for suppressing the expression of a target gene, comprising:

administering an RNA duplex to a subject or an expression system in vivo, in vitro or ex vivo, the RNA duplex comprising a passenger strand and a guide strand for a target RNA that is at least a portion of mRNA of the target gene, wherein both ends of the double-stranded RNA formed by pairing the passenger strand and the guide strand form blunt ends, wherein the passenger strand comprises two units represented by formula (2) at each of the 5' and 3' ends, and the guide strand comprises two units represented by formula (2) at the 3' end, (2)

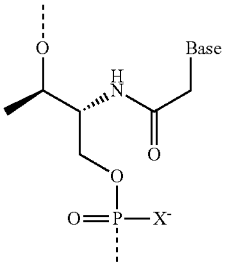

where X represents an oxygen atom or a sulfur atom.

5. A target RNA detection agent comprising an antisense strand for the target RNA, the antisense strand comprising:

a hybridization region comprising units represented by formula (1) capable of specifically hybridizing to the target RNA;

a stem region comprising units represented by formula (1), directly linked to 3' end and 5' end of the hybridization region, respectively, and hybridizing to form a loop around the hybridization region;

a signal element indicating that the hybridization region has hybridized to the target RNA; and one or two diaminopurine-containing units having 2,6-diaminopurine as a base instead of one or two adenine-units having an adenine base in the hybridization region, the adenine-containing units being spaced one to three bases from the 3' end and 5' end of the hybridization region, (1)

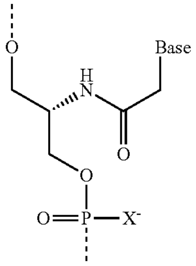

where X represents an oxygen atom or a sulfur atom.

6. The target RNA detection agent of claim 5, wherein the target RNA is miR21.

7. The target RNA detection agent of claim 6, wherein the hybridizing region and the stem region have a continuous base sequence represented by SEQ ID NO: 21.

8. The target RNA detection agent of claim 5, wherein the target RNA is mRNA of EGFR gene and is for detecting a single-base substitution in the gene.

9. The target RNA detection agent of claim 8, wherein the hybridizing region and the stem region have a continuous base sequence selected from the base sequences represented by SEQ ID NOs: 14 to 20.

* * * * *

```
                    SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: siRNA

<400> SEQUENCE: 1

ggaaugccac agacgaagut t                                    21


<210> SEQ ID NO 2
<211> LENGTH: 21
<212> TYPE: DNA
<213> ORGANISM: Artificial Sequence
<220> FEATURE:
<223> OTHER INFORMATION: siRNA

<400> SEQUENCE: 2
```

-continued acuucgucug uggcauucct t 21

<210> SEQ ID NO 3
<211> LENGTH: 23
<212> TYPE: RNA
<213> ORGANISM: Artificial Sequence
<220> FEATURE:
<223> OTHER INFORMATION: siRNA

<400> SEQUENCE: 3
aaggaaugcc acagacgaag uga 23

<210> SEQ ID NO 4
<211> LENGTH: 23
<212> TYPE: DNA
<213> ORGANISM: Artificial Sequence
<220> FEATURE:
<223> OTHER INFORMATION: siRNA

<400> SEQUENCE: 4
ucacuucguc uguggcauuc cut 23

<210> SEQ ID NO 5
<211> LENGTH: 23
<212> TYPE: RNA
<213> ORGANISM: Artificial Sequence
<220> FEATURE:
<223> OTHER INFORMATION: siRNA

<400> SEQUENCE: 5
aaggaaugcc acagacgaag uga 23

<210> SEQ ID NO 6
<211> LENGTH: 23
<212> TYPE: DNA
<213> ORGANISM: Artificial Sequence
<220> FEATURE:
<223> OTHER INFORMATION: siRNA

<400> SEQUENCE: 6
ucacuucguc uguggcauuc ctt 23

<210> SEQ ID NO 7
<211> LENGTH: 23
<212> TYPE: RNA
<213> ORGANISM: Artificial Sequence
<220> FEATURE:
<223> OTHER INFORMATION: siRNA

<400> SEQUENCE: 7
aaggaaugcc acagacgaag uga 23

<210> SEQ ID NO 8
<211> LENGTH: 23
<212> TYPE: DNA
<213> ORGANISM: Artificial Sequence
<220> FEATURE:
<223> OTHER INFORMATION: siRNA

<400> SEQUENCE: 8
ucacuucguc uguggcauuc cut 23

<210> SEQ ID NO 9
<211> LENGTH: 23
<212> TYPE: RNA
<213> ORGANISM: Artificial Sequence -continued
<220> FEATURE:
<223> OTHER INFORMATION: siRNA

<400> SEQUENCE: 9
aaggaaugcc acagacgaag uga 23

<210> SEQ ID NO 10
<211> LENGTH: 23
<212> TYPE: DNA
<213> ORGANISM: Artificial Sequence
<220> FEATURE:
<223> OTHER INFORMATION: siRNA

<400> SEQUENCE: 10
ucacuucguc uguggcauuc ctt 23

<210> SEQ ID NO 11
<211> LENGTH: 12
<212> TYPE: DNA
<213> ORGANISM: Artificial Sequence
<220> FEATURE:
<223> OTHER INFORMATION: Gapmer Type Antisence Nucleic Acid

<400> SEQUENCE: 11
ggcatgagct tc 12

<210> SEQ ID NO 12
<211> LENGTH: 30
<212> TYPE: RNA
<213> ORGANISM: Homo sapiens

<400> SEQUENCE: 12
ccgugcagcu caucaugcag cucaugcccu 30

<210> SEQ ID NO 13
<211> LENGTH: 30
<212> TYPE: RNA
<213> ORGANISM: Homo sapiens

<400> SEQUENCE: 13
ccgugcagcu caucacgcag cucaugcccu 30

<210> SEQ ID NO 14
<211> LENGTH: 24
<212> TYPE: DNA
<213> ORGANISM: Artificial Sequence
<220> FEATURE:
<223> OTHER INFORMATION: Molecular Beacon Probe

<400> SEQUENCE: 14
tgcagcgctg cgtgatgagc tgca 24

<210> SEQ ID NO 15
<211> LENGTH: 23
<212> TYPE: DNA
<213> ORGANISM: Artificial Sequence
<220> FEATURE:
<223> OTHER INFORMATION: Molecular Beacon Probe

<400> SEQUENCE: 15
tgcaggctgc gtgatgagct gca 23

<210> SEQ ID NO 16
<211> LENGTH: 21
<212> TYPE: DNA

-continued

<213> ORGANISM: Artificial Sequence
<220> FEATURE:
<223> OTHER INFORMATION: Molecular Beacon Probe

<400> SEQUENCE: 16
cagctgctgc gtgatgagct g 21

<210> SEQ ID NO 17
<211> LENGTH: 19
<212> TYPE: DNA
<213> ORGANISM: Artificial Sequence
<220> FEATURE:
<223> OTHER INFORMATION: Molecular Beacon Probe

<400> SEQUENCE: 17
gctcagctgc gtgatgagc 19

<210> SEQ ID NO 18
<211> LENGTH: 24
<212> TYPE: DNA
<213> ORGANISM: Artificial Sequence
<220> FEATURE:
<223> OTHER INFORMATION: Molecular Beacon Probe

<400> SEQUENCE: 18
tgcagcgctg catgatgagc tgca 24

<210> SEQ ID NO 19
<211> LENGTH: 23
<212> TYPE: DNA
<213> ORGANISM: Artificial Sequence
<220> FEATURE:
<223> OTHER INFORMATION: Molecular Beacon Probe

<400> SEQUENCE: 19
tgcaggctgc atgatgagct gca 23

<210> SEQ ID NO 20
<211> LENGTH: 21
<212> TYPE: DNA
<213> ORGANISM: Artificial Sequence
<220> FEATURE:
<223> OTHER INFORMATION: Molecular Beacon Probe

<400> SEQUENCE: 20
cagctgctgc atgatgagct g 21

<210> SEQ ID NO 21
<211> LENGTH: 28
<212> TYPE: DNA
<213> ORGANISM: Artificial Sequence
<220> FEATURE:
<223> OTHER INFORMATION: Molecular Becon Probe
<220> FEATURE:
<221> NAME/KEY: modified_base
<222> LOCATION: (6)..(6)
<223> OTHER INFORMATION: n is 2,6-diaminopurine
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: modified_base
<222> LOCATION: (7)..(7)
<223> OTHER INFORMATION: n is 2,6-diaminopurine
<220> FEATURE:
<221> NAME/KEY: modified_base
<222> LOCATION: (20)..(20)
<223> OTHER INFORMATION: n is 2,6-diaminopurine -continued

```
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: modified_base
<222> LOCATION: (21)..(21)
<223> OTHER INFORMATION: n is 2,6-diaminopurine

<400> SEQUENCE: 21

gcgtcnncat cagtctgatn ngctacgc                                    28


<210> SEQ ID NO 22
<211> LENGTH: 22
<212> TYPE: RNA
<213> ORGANISM: Homo sapiens

<400> SEQUENCE: 22

uagcuuauca gacugauguu ga                                          22
```